United States Patent
Yamazaki et al.

[11] Patent Number: 5,935,977
[45] Date of Patent: Aug. 10, 1999

[54] SUBSTITUTED VINYL PYRIDINE DERIVATIVE AND DRUGS CONTAINING THE SAME

[75] Inventors: Kazuo Yamazaki, Sawara; Yoichiro Ogawa, Chiba; Hidehiko Kohya, Narita; Tadashi Mikami, Sawara; Noriyuki Kawamoto; Noriaki Shioiri, both of Narita; Hiroshi Hasegawa, Sakura; Susumu Sato, Narita, all of Japan

[73] Assignee: SS Pharmaceutical Co., Ltd., Tokyo, Japan

[21] Appl. No.: 09/068,986

[22] PCT Filed: Sep. 22, 1997

[86] PCT No.: PCT/JP97/03354

§ 371 Date: May 26, 1998

§ 102(e) Date: May 26, 1998

[87] PCT Pub. No.: WO98/13348

PCT Pub. Date: Apr. 2, 1998

[30] Foreign Application Priority Data

Sep. 25, 1996 [JP] Japan ................................ 8-252944

[51] Int. Cl.[6] .................. C07D 213/69; A61K 31/44
[52] U.S. Cl. ............................. 514/348; 546/296
[58] Field of Search .............................. 546/296; 514/348

[56] References Cited

FOREIGN PATENT DOCUMENTS 157420  9/1985  European Pat. Off. .

WO97/33870  9/1997  WIPO .

OTHER PUBLICATIONS

Lee et al, Circ. Shock, vol. 44(3) pp. 97–103, 1995.

*Primary Examiner*—Zinna Northington Davis
*Attorney, Agent, or Firm*—Oblon, Spivak, McClelland, Maier & Neustadt, P.C.

[57] ABSTRACT

The present invention relates to a substituted vinylpyridine derivative represented by the following formula (1):

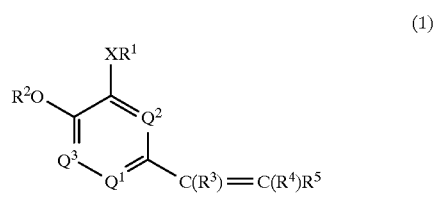

(wherein $R^1$ represents a hydrogen atom, an alkyl group, etc., $R^2$ represents an alkyl group; one of $R^3$ and $R^4$, which are different from each other, represents a hydrogen atom and the other represents a nitrile group, $R^5$ represents an aryl group or a heteroaryl group, X represents an oxygen atom, etc., and one of $Q^1$, $Q^2$, and $Q^3$ represents a nitrogen atom and the other two represent CH); a salt of the derivative; and a drug containing the derivative or salt as the active ingredient. Due to strong PDE inhibitory action and TNF-α production inhibitory action, the derivative, salt, and drug are useful for the prevention and treatment of a wide variety of inflammatory diseases and autoimmune diseases.

8 Claims, No Drawings

SUBSTITUTED VINYL PYRIDINE DERIVATIVE AND DRUGS CONTAINING THE SAME

This application is a 371 of PCT/JP97/03354, filed Sep. 22, 1997.

TECHNICAL FIELD

The present invention relates to a novel substituted vinylpyridine derivative and salts thereof, which are endowed with strong and selective phosphodiesterase (PDE) IV inhibitory action and strong inhibitory action against production of the tumor necrotizing factor (TNF-α), as well as with high safety. The invention also relates to drugs containing the derivative or salts and useful for the prevention and treatment of a broad range of inflammatory diseases and autoimmune diseases.

BACKGROUND ART

PDE is an enzyme which acts as a catalyst in hydrolysis of cyclic adenosine 3',5'-phosphate (cAMP) or cyclic guanosine 3',5'-phosphate (cGMP) into 5'-monophosphate. cAMP and cGMP are produced from ATP and GTP, respectively, following activation of adenylate cyclase or guanylate cyclase in response to a hormone or chemical transmission substance, and work as intracellular second messengers. PDE inhibitory agents block the activity of PDE to increase the amounts of intracellular cAMP and cGMP, to thereby suppress cellular response. At present, PDE is known to have type I to type VIII isozymes. These are found in the central nervous system, circulatory system, respiratory system, digestive system, reproductive system, and blood cell system. The distribution of these isozymes differs according to the tissue. This suggests that a PDE-isozyme-specific inhibitor may increase the amount of cAMP in certain specific tissue.

In recent years, considerable efforts have been devoted to research and development of highly specific PDE isozyme inhibitors. For example, attempts have been made to develop drugs that exhibit organ specificity attributable to localization of respective isozymes. As a result of such attempts, PDE IV is considered to be a potential agent effective for both asthmatic attack and chronic respiratory tract inflammation, due to the facts that PDE IV is present predominantly in the airway tissue or inflammatory cells, such as eosinocytes and neutrophilic leukocytes, which are intimately related to asthmatic symptoms and that drugs that inhibit the action of PDE IV exhibit bronchodilatation action as well as inhibitory action against activation of inflammatory leukocytes. Thus, active studies have been performed worldwide focusing on development of a selective inhibitor against PDE IV as a new remedy for bronchial asthma.

PDE IV, which also exists in the central nervous system, is expected to improve memory and mitigate anxiety, based on the consideration that a rolipram, a selective PDE IV inhibitor, specifically localizes in the brain tissue to increase noradrenergic nervous transmission on a synapse or post-synapse level in response to an increased amount of cAMP, which is a second messenger of noradrenalin.

TNF-α is a cytokine produced by an activated macrophage. Although TNF-α was first discovered to be a factor which induces hemorrhagic necrosis in a tumor site, it is now recognized as a mediator which widely participates in inflammatory reactions and the immune mechanism. Excessive production of TNF-α, however, induces disorders in tissue to cause a variety of pathological conditions. Rapid release of TNF-α induced by intracellular toxins is responsible for the lethality.

TNF-α promotes production of platelet-activating factor (PAF), a variety of inflammatory arachidonic metabolites, and activated oxygen. Moreover, it induces production of interleukin (IL)-1, IL-6, and IL-8. As is understood from this, excessive production of TNF-α aggravates inflammatory reactions and, in the case of chronic inflammatory diseases such as rheumatism, osteoporosis, and terminal cancers, results in a persistence of complication of diseases, in which the concentrations of these cytokines are maintained consistently so as exacerbate the symptoms. Accordingly, in pathological conditions in which TNF-α is produced excessively, control of its release is strongly sought by clinicians.

So far, molecular design of a selective PDE IV inhibitor has not yielded satisfactory results, and therefore limitation is imposed on use of the selective PDE IV inhibitor. Theophylline, which is a xanthine-based drug widely used by clinicians as a therapeutic agent for the treatment of bronchial asthma, exhibits bronchodilating action stemming from the adenosine antagonizing action and PDE inhibitory action. However, theophylline sometimes causes adverse side effects in the circulatory system and central nervous system, as it inhibits PDE non-selectively. Thus, the safety range of theophylline is rather narrow. Rolipram and Ro20-1724 selectively inhibit PDE IV at a potency 100 times that at which they inhibit other PDE isozymes. However, the inhibitory power itself is not significant, imposing limitations on applicable diseases.

TNF-α production inhibitors include antiphlogistic steroids, antihistaminic agents, PAF antagonists, and active-oxygen quencher. However, these are nonspecific inhibitors with either weak power or, when their power is strong, with low tissue specificity, thus limiting their methods of use. Moreover, protease inhibitors have recently been reported to be specific TNF-α production inhibitors. The protease inhibitors are peptide derivatives and have not yet been extensively studied with regard to administration methods, etc.

Accordingly, the present invention is directed to the provision of therapeutics for a variety of diseases based on the selective PDE IV inhibitory action; the provision of therapeutics for a variety of diseases based on the TNF-α production inhibitory action; and the provision of drugs for the prevention and treatment of a wide variety of inflammatory diseases and autoimmune diseases, which drugs are designed based on concurrent actions of these two actions and are endowed with enhanced effects, higher specificity, and higher safety.

DISCLOSURE OF THE INVENTION

Under the above circumstances, the present inventors synthesized numerous compounds, and studied their PDE inhibitory action and inhibitory action against production of a variety types of cytokines, and as a result found that the new substituted vinylpyridine derivatives represented by formula (1) or salts thereof potently and selectively inhibit PDE IV only, while not acting on other PDE isozymes, and that production of TNF-α is potently inhibited. As a result, the below-described substituted vinylpyridine derivatives have been shown to be effective for the prevention and treatment of the aforementioned wide ranges of inflammatory diseases, autoimmune diseases, and other diseases associated with disturbed matabolism of the cerebrum. The present invention has been completed based on these findings.

Accordingly, the present invention provides a substituted vinylpyridine derivative represented by the following formula (1):

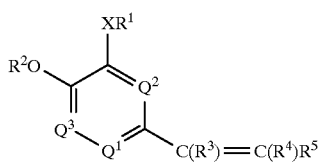
(1)

wherein $R^1$ represents a hydrogen atom, an alkyl group, an alkenyl group, a hydroxyalkyl group which may have a substituent, an alkoxyalkyl group, an alkoxycarbonyl alkyl group, an alkoxyalkoxyalkyl group, an aminoalkyl group which may have a substituent, a saturated heterocyclic group which may have a substituent, an aralkyl group which may have a substituent, a benzocycloalkyl group which may have a substituent, or an alkyl group having a heterocyclic group which may have a substituent; $R^2$ represents an alkyl group; one of $R^3$ and $R^4$, which are different from each other, represents a hydrogen atom and the other represents a nitrile group, a carboxyl group, or an alkoxycarbonyl group; $R^5$ represents a monocyclic or ring-condensed aryl group which may have a substituent or a monocyclic or ring-condensed heteroaryl group which may have a substituent; X represents an oxygen atom or a sulfur atom; and one of $Q^1$, $Q^2$, and $Q^3$ represents a nitrogen atom and the other two represent CH; as well as a salt of the derivative, a hydrate of the derivative, or an N-oxide of the derivative.

The present invention also provides a drug containing as the active ingredient a substituted vinylpyridine derivative represented by the above-described formula (1), a salt thereof, a hydrate thereof, or an N-oxide thereof.

The present invention also provides a pharmaceutical composition containing a substituted vinylpyridine derivative represented by the above-described formula (1), a salt thereof, a hydrate thereof, or an N-oxide thereof; and a pharmacologically acceptable carrier.

The present invention further provides use, as a drug, of a substituted vinylpyridine derivative represented by the above-described formula (1), a salt thereof, a hydrate thereof, or an N-oxide thereof.

The present invention still further provides a preventive or therapeutic method for a disease caused by the production of PDE IV or TNF-α, which method comprises the step of administering to a mammal including a human an effective amount of a substituted vinylpyridine derivative represented by the above-described formula (1), a salt thereof, a hydrate thereof, or an N-oxide thereof.

BEST MODE FOR CARRYING OUT THE INVENTION

In the substituted vinylpyridine derivative of formula (1) of the present invention, examples of alkyl groups represented by $R^1$ include C1–12 linear, branched, cyclic, cyclic-linear, or cyclic-branched alkyl groups. Of these, linear or branched alkyl groups are preferably C1–8 alkyl groups, and examples include methyl, ethyl, n-propyl, i-propyl, n-butyl, i-butyl, n-pentyl, i-pentyl, n-hexyl, n-heptyl, and n-octyl. Cyclic alkyl groups are preferably C3–8 cycloalkyl groups, and examples include cyclopropyl, cyclobutyl, cyclopentyl, cyclohexyl, cycloheptyl, and norbornyl. Cyclic-linear or cyclic-branched alkyl groups are preferably C4–12 alkyl groups, and examples include cyclopropylmethyl, cyclobutylmethyl, cyclopentylmethyl, cyclopropylethyl, cyclobutylethyl, and cyclopentylethyl.

Examples of alkenyl groups include C2–12 linear, branched, or cyclic alkenyl groups. Of these, C5–8 cyclic alkenyl groups are preferred, and examples include 3-cyclopentenyl, 2-cyclohexenyl, 3-cyclohexenyl, 4-cycloheptenyl, and norbornenyl.

Hydroxyalkyl groups may be linear, branched, or cyclic, and may be substituted with one or more hydroxy groups. Hydroxyalkyl groups have preferably 2–12 carbon atoms, more preferably 2–8 carbon atoms. Examples of liner or branched hydroxyalkyl groups include 2-hydroxyethyl, 3-hydroxypropyl, 4-hydroxybutyl, 5-hydroxypentyl, and 6-hydroxyhexyl. Cyclic hydroxyalkyl groups are preferably C4–8 hydroxycycloalkyl groups, and examples include 3-hydroxycyclobutyl, 3-hydroxycyclopentyl, 3-hydroxycyclohexyl, and 4-hydroxycyclohexyl. Dihydroxyalkyl groups are preferably C3–7 dihydroxyalkyl groups, and examples include 1,3-dihydroxy-2-propyl, 1,5-dihydroxypentyl, and 1,7-dihydroxyheptyl. A hydroxy group of these hydroxyalkyl groups may be substituted with an alkoxycarbonyl group, an acyl group, or a TBS (t-butyldimethylsilyl) group.

Alkoxyalkyl groups are preferably those whose total carbon number is 2–12, and examples include methoxymethyl, methoxyethyl, and ethoxyethyl.

Alkoxyalkoxyalkyl groups are preferably those whose total carbon number is 3–12, and examples include methoxyethoxymethyl.

Alkoxycarbonylalkyl groups are preferably those whose total carbon number is 3–13, and examples include methoxycarbonylmethyl and ethoxycarbonylethyl.

Examples of aminoalkyl groups which may be substituted include C2–12 linear or branched aminoalkyl or diaminoalkyl groups. Of these, C2–8 linear or branched aminoalkyl groups are preferred, and examples include 2-aminoethyl, 3-aminopropyl, 4-aminobutyl, 5-aminopentyl, and 6-aminohexyl. Diaminoalkyl groups are preferably those having 3–7 carbon atoms, and examples include 1,3-diamino-2-propyl, 1,5-diaminopentyl, and 1,7-diaminoheptyl. An amino group of these aminoalkyl groups may be substituted with an alkoxycarbonyl group, an acyl group, etc.

Saturated heterocyclic groups include a 5–6-membered heterocycle having an oxygen atom, a sulfur atom, or a nitrogen atom as a hetero atom. Examples of these include 2-tetrahydropyranyl, 3-tetrahydropyranyl, 2-tetrahydrofuranyl, and 3-tetrahydrofuranyl.

Examples of aralkyl groups which may be substituted include benzyl, phenethyl, phenylpropyl, and phenylbutyl; benzyl, phenethyl, and phenylpropyl having one or plurality of methoxy group(s), alkoxycarbonyl group(s), or alkylenedioxy group(s) at o-, m-, and/or p-position. The alkoxy groups preferably have 1–6 carbon atom(s), and examples include methoxy, ethoxy, n-propoxy, and i-propoxy.

Benzocycloalkyl groups which may be substituted have 9–11 carbon atoms, and examples include 1-indanyl, 2-indanyl, 1,2,3,4-tetrahydro-1-naphthyl and 1,2,3,4-tetrahydro-2-naphthyl.

Examples of alkyl groups which may have a (optionally substituted) heterocyclic group include C1–5 linear alkyl groups substituted with an aromatic heterocycle, a saturated heterocycle, or an unsaturated heterocycle. Of these, aromatic heterocycles may be 5- or 6-membered heteroaryl groups having 1–3 nitrogen atom(s), oxygen atom(s), or sulfur atom(s), and examples include 2-pyridyl, 3-pyridyl, 4-pyridyl, 2-pyrimidyl, 2-pyrazyl, 2-thiazolyl, 5-thiazolyl, 4-methyl-5-thiazolyl, 1-imidazolyl, 2-imidazolyl, 3-imidazolyl, 2-oxazolyl, 2-thienyl, 3-thienyl, and 2-furanyl. Saturated or unsaturated heterocycles may be 5–7-member groups having 1–3 nitrogen atom(s), oxygen atom(s), or sulfur atom(s), and examples include 1-pyrrolidyl, 1-piperidyl, 1-azepanyl, 1-morpholino, pyrrolidin-2-on-1-yl, and pyridin-2-on-1-yl.

Substituents in benzocycloalkyl groups or a heterocyclic group of heterocycle-substituted alkyl groups may be 1–3 group(s) selected from hydroxy, halogeno, C1–6 alkyl, C1–6 alkoxy, C1–6 halogenoalkyl, cyano, and nitro.

Alkyl groups represented by $R^2$ preferably have 1–6 carbon atom(s), and examples include methyl, ethyl, n-propyl, i-propyl, n-butyl, i-butyl, sec-butyl, and tert-butyl.

Alkoxy groups of alkoxycarbonyl groups represented by $R^3$ and $R^4$ preferably have 1–6 carbon atom(s), and examples include methoxy, ethoxy, n-propoxy, and i-propoxy.

Examples of monocyclic (optionally substituted) aryl groups represented by $R^5$ include a phenyl group which may be substituted with 1–3 group(s) selected from halogeno, C1–6 alkyl, C1–6 alkoxy, C1–6 halogenoalkyl, C1–6 alkoxycarbonyl, carboxyl, cyano, and nitro. Examples of these include phenyl, 2-fluorophenyl, 2-chlorophenyl, 2-bromophenyl, 2-methylphenyl, 2-ethylphenyl, 2-i-propylphenyl, 2-t-butylphenyl, 2-methoxyphenyl, 2-trifluoromethylphenyl, 2-cyanophenyl, 2-nitrophenyl, 2-carboxyphenyl, 2-methoxycarbonylphenyl, 2-ethoxycarbonylphenyl, 3-carboxyphenyl, 3-methoxycarbonylphenyl, 3-ethoxycarbonylphenyl, 4-fluorophenyl, 4-chlorophenyl, 4-bromophenyl, 4-trifluoromethylphenyl, 4-cyanophenyl, 4-nitrophenyl, 4-carboxyphenyl, 4-methoxycarbonylphenyl, 4-ethoxycarbonylphenyl, 2,6-difluorophenyl, 2,6-dichlorophenyl, 2,6-dibromophenyl, 2,6-dimethylphenyl, 2,6-dimethoxyphenyl, and 2,6-ditrifluoromethylphenyl.

Examples of condensed-ring (optionally substituted) aryl groups include a naphthyl group which may be substituted with 1–3 group(s) selected from halogeno, C1–6 alkyl, C1–6 alkoxy, C1–6 halogenoalkyl, C1–6 alkoxycarbonyl, carboxyl, cyano, and nitro. Examples of these include 1-naphthyl, 2-naphthyl, 2-chloro-1-naphthyl, and 2-methoxy-1-naphthyl.

Examples of monocyclic (optionally substituted) heteroaryl groups include a 5–6-membered heteroaryl group (having 1–3 atom(s) of nitrogen, oxygen, or sulfur) which may be substituted with 1–3 group(s) selected from halogeno, C1–6 alkyl, C1–6 alkoxy, C1–6 halogenoalkyl, C1–6 alkoxycarbonyl, carboxyl, cyano, and nitro. Examples of these include 2-pyridyl, 3-pyridyl, 4-pyridyl, 2-carboxy-4-pyridyl, 2-methoxycarbonyl-4-pyridyl, 2-ethoxycarbonyl-4-pyridyl, 3-chloro-4-pyridyl, 3-bromo-4-pyridyl, 3-methoxy-4-pyridyl, 3,5-dichloro-4-pyridyl, 3,5-dibromo-4-pyridyl, 3,5-dimethoxy-4-pyridyl, 3-chloro-5-methoxy-4-pyridyl, 2-pyrimidyl, 2-pyrazyl, 2-thienyl, 3-thienyl, and 2-furanyl.

Examples of condensed-ring (optionally substituted) heteroaryl groups include a condensed-ring heteroaryl group (containing a nitrogen atom) which may be substituted with 1–3 group(s) selected from halogeno, C1–6 alkyl, C1–6 alkoxy, C1–6 halogenoalkyl, C1–6 alkoxycarbonyl, carboxyl, cyano, and nitro. Examples of these include 2-quinolyl, 4-quinolyl, and 1-isoquinolyl.

Examples of salts or hydrates of the substituted vinylpyridine derivative of formula (1) of the present invention include hydrochlorides, nitrates, hydrobromides, p-toluenesulfonates, methanesulfonates, fumarates, maleates, malonates, succinates, citrates, tartarates, and hydrates thereof. Examples of N-oxides of the substituted vinylpyridine derivative inculde pyridine-N-oxides and N-oxides of a monocyclic or condensed-ring heteroaryl group represented by $R^5$.

The substituted vinylpyridine derivative of the present invention is prepared by, for example, the following reaction scheme. Briefly, a known compound (2) is easily derived from kojic acid (which is inexpensive and available in large quantities) through two or three reactions (Step 1); the known compound (2) is processed to yield a key intermediate (3) or (4) of the synthesis of the present invention (Step 2 or 3); and the intermediate is condensed through reaction with commercially available (or separately synthesized) arylaldehydes ($R^5$-CHO), arylacetonitriles or arylacetate esters ($R^5$-$CH_2R^7$) to thereby obtain a compound (1a) of the present invention.

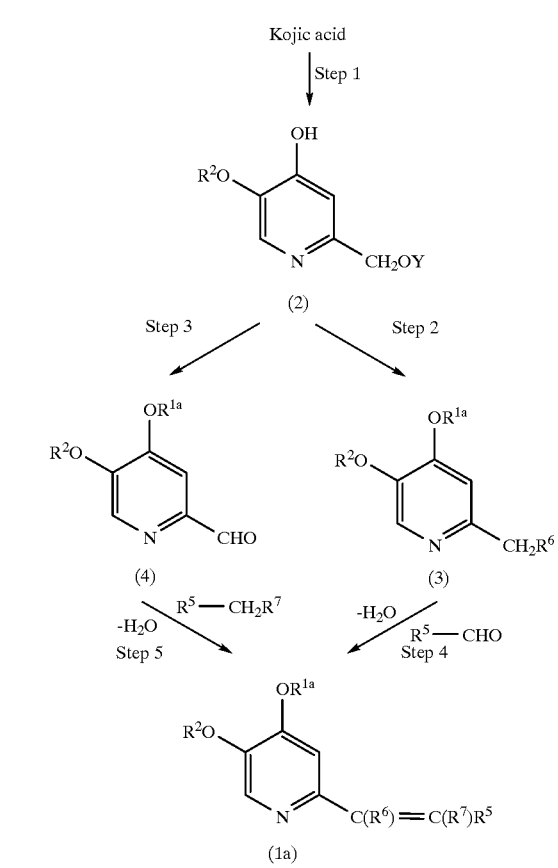

wherein one of $R^6$ and $R^7$, which are different from each other, represents a hydrogen atom and the other represents a nitrile group or an alkoxycarbonyl group; Y represents a hydrogen atom or a protective group (preferably benzyl or tetrahydro-2-pyranyl); $R^2$ and $R^5$ have the same meanings as described above; $R^{1a}$ is identical to $R^1$ except when $R^1$ is a hydrogen atom, with the presence of a protective group being preferred when $R^{1a}$ is a hydroxyalkyl group.

In other words, the key intermediate (3) is reacted with $R^5$-CHO (Step 4) or the key intermediate (4) is reacted with $R^5$-$CH_2R^7$ (Step 5) to thereby obtain a compound (1a). These reactions easily proceed in the presence of a base such as sodium alkoxide, sodium amide, alkali hydroxide, alkyllithium, or a tertiary alkylamine. These reactions are preferably conducted in methanol with sodium methoxide or in ethanol with sodium ethoxide in the temperature range from 0° C. to room temperature.

The above-described key intermediate (3) may be easily obtained from the known compound (2) through the following reaction scheme.

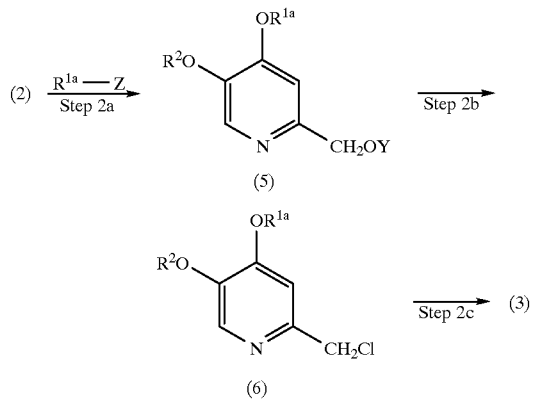

wherein $R^{1a}$ and $R^2$, and Y have the same meanings as described above and Z represents a leaving group (typically a halogen atom).

The compound (2) is reacted with halide reagents ($R^{1a}$-Z) to obtain a compound (5). If the compound (5) is having a protective group in Y, then it is de-protected and a compound (5: Y=a hydrogen atom) is derived therefrom (Step 2a). Alternatively, the compound (2: Y=a protective group) is converted to the compound (5: Y=protective group) by Mitsunobu reaction with primary or secondary alcohols and the protective group is removed to thereby obtain the compound (5: Y=a hydrogen atom). Next, the compound (5: Y=a hydrogen atom) is converted to a chloro compound (6) (Step 2b). The compound (6) is further reacted with M-CN to obtain the key intermediate (3: $R^6$=a nitrile group), whose nitrile group undergoes an alcoholysis to obtain the other key intermediate (3: $R^6$=an alkoxycarbonyl group) (Step 2c).

Reactions of Step 2a are preferably carried out in a solvent such as an alcohol, tetrahydrofuran, dimethylformamide, or dimethyl sulfoxide in the presence of a base such as potassium carbonate, sodium carbonate, or, in some cases, potassium iodide, or sodium iodide in the temperature range from room temperature to 80° C.; or in a water-alcohol mixed solvent in the presence of sodium hydroxide or potassium hydroxide as a base in the temperature range from 0° C. to the reflux temperature. Also, the reaction between the compound (2: Y=a protective group) and $R^{1a}$-Z proceeds easily, under conditions other than the above-described reaction conditions, i.e., in a solvent such as terahydrofuran, 1,2-dimethoxyethane, dioxane, dimethylformamide, or dimethyl sulfoxide in the presence of sodium hydride or potassium hydride as a base in the temperature range from 0° C. to room temperature. The reaction between the compound (2: Y=a protective group) and primary or secondary alcohols easily proceeds to yield the compound (5: Y=a protective group) by the typical conditions of Mitsunobu reaction, i.e., in the presence of diethyl azodicarboxylate and triphenylphosphine.

In Step 2a, preferred examples of substituents of $R^{1a}$ include alkyl, cycloalkyl, cycloalkylalkyl, hydroxyalkyl, and (optionally substituted) aralkyl. By Mitsunobu reaction to obtain the compound (5: Y=a protective group), a substituent such as cycloalkyl, cycloalkenyl, heterocycloalkyl, or benzocycloalkyl is preferred.

When the compound (5: Y=a protective group) is de-protected, there are employed conditions such as hydrogenation by use of a catalyst such as palladium or Raney nickel; reductive removal by use of a compound such as ammonium formate, cyclopentene, or 1,4-cyclohexadiene (for benzyl-substituted compound); or hydrolysis in a water-organic solvent with a mineral acid or an organic acid (for tetrahydro-2-pyranyl compound).

The reaction between thionyl chloride and the compound (5) proceeds easily without or within a solvent inert to thionyl chloride at room temperature to obtain the chloro compound (6) from the compound (5: Y=a hydrogen atom) (Step 2b).

Step 2c, in which the key intermediate (3: $R^6$=a nitrile group) is obtained from the chloro compound (6), is preferably carried out in a polar and aprotic solvent such as dimethyl sulfoxide or dimethylformamide in the presence of sodium cyanide in the temperature range from room temperature to 100° C. The also reaction is easily performed through the cyano-anion-activation method using a phase transfer catalyst or crown ether.

The key intermediate (3: $R^6$=an alkoxycarbonyl group) is obtained from the key intermediate (3: $R^6$=a nitrile group) through conversion of the nitrile group in hydrogen—chloride-gas-saturated methanol or a lower alcohol in the temperature range from room temperature to the reflux temperature.

The above-described key intermediate (4) may be easily obtained from the known compound (2) through the following reaction scheme.

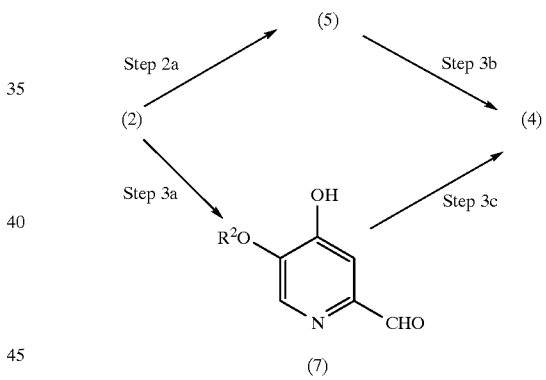

wherein $R^2$ has the same meaning as described above.

The formyl compound (4) is obtained through conversion of the compound (5) obtained in the above-described Step 2a by use of an oxidant (Step 3b); or through oxidation of the compound (2) to obtain a compound (7) (Step 3a), followed by reaction with the halide reagent ($R^{1a}$-Z) (Step 3c).

Step 3a, in which the compound (7) is obtained from the compound (2), is preferably carried out in a solvent such as tetrahydrofuran, 1,4-dioxane, or dimethylformamide with an excessive amount of active manganese dioxide or nbarium manganate(VI) as an oxidant in the temperature range from room temperature to 100° C.

Step 3b, in which the formyl compound (4) is obtained from the compound (5), is easily carried out in a solvent such as chloroform, dichloromethane, or acetone with an excessive amount of active manganese dioxide or barium manganate(VI) as an oxidant in the temperature range from room temperature to the reflux temperature; or through oxidation by a dimethyl sulfoxide/sulfur trioxide-pyridine-complex (Parikh-Doering method) or oxidation by a dimethyl sulfoxide/oxalyl chloride (Swern method). Also, the formyl compound (4) may be obtained through oxidation by pyridinium chlorochromate (PCC) or pyridinium dichromate (PDC).

Step 3c, in which the formyl compound (4) is obtained from the compound (7), is carried out through reaction with $R^{1a}$-Z in a solvent such as tetrahydrofuran, 1,2-dimethoxyethane, dimethylformamide, or dimethyl sulfoxide with a base such as sodium hydride or potassium hydride in the temperature range from 0° C. to room temperature; or in a solvent such as an alcohol, tetrahydrofuran, dimethylformamide, or dimethyl sulfoxide with a base such as potassium carbonate or sodium carbonate, or in some cases, potassium iodide or sodium iodide in the temperature range from 0° C. to 80° C.

The compound (1b') or (1b") of the present invention is obtained through removal of an oxyalkyl group from the compound (1a) of the present invention having a methoxymethyl or methoxyethoxymethyl group as $R^1$ and a hydrogen atom as $R^7$ (1a') or as $R^6$ (1a").

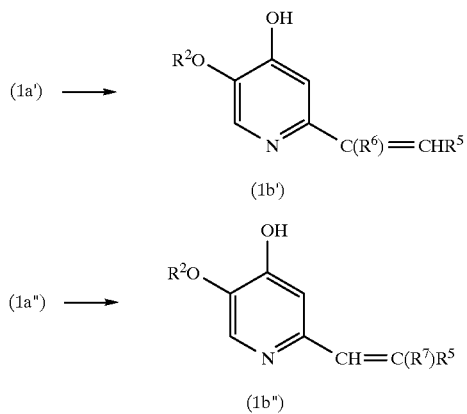

wherein $R^2$, $R^5$, $R^6$, and $R^7$ have the same meanings as described above.

De-protection of the compound (1a') or (1a") of the present invention is carried out by use of trifluoroacetic acid or diluted acetic acid (for $R^1$=a methoxymethyl group) or trifluoroacetic acid (for $R^1$=a methoxyethoxymethyl group).

The compound (1c') or (1c") of the present invention is obtained through hydrolysis of the compound (1a) of the present invention having an alkoxycarbonyl group as $R^6$ and a hydrogen atom as $R^7$ (1a'''), or a hydrogen atom as $R^6$ and an alkoxycarbonyl group as $R^7$ (1a"").

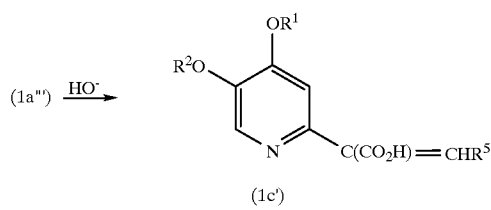

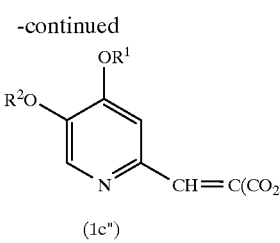

wherein $R^1$, $R^2$ and $R^5$ have the same meanings as described above.

The above hydrolysis reaction is carried out under alkaline conditions through a widely employed method in which hydrolysis is allowed to proceed in a lower alcohol, by use of diluted NaOH aqueous solution or diluted KOH aqueous solution in a temperature range from room temperature to reflux temperature.

Compound (1a) may also be obtained by reacting compound (1b') or (1b") of the present invention with a halide reagent ($R^{1a}$-Z) in the presence of a base, or alternatively, by Mitsunobu reaction between compound (1b') or (1b") and a primary or secondary alcohol ($R^{1a}$-OH).

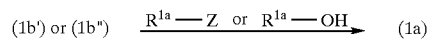

The substituent-introduction reaction by use of a halide reagent ($R^{1a}$-Z) is carried out in a solvent such as alcohol, tetrahydrofuran, dimethylformamide, or dimethyl sulfoxide, in the presence of a base such as potassium carbonate or sodium carbonate, or in some cases potassium iodide or sodium iodide, in a temperature range from room temperature to 80° C. Alternatively, this reaction is carried out in a solvent such as tetrahydrofuran, 1,2-dimethoxyethane, dioxane, dimethylformamide, or dimethyl sulfoxide, by use of sodium hydride or potassium hydride as a base, in a temperature range from 0° C. to room temperature. The substituent-introduction reaction through use of a primary or secondary alcohol ($R^{1a}$-OH) proceeds easily by the typical conditions of Mitsunobu reaction; i.e., in the presence of diethyl azodicarboxylate and triphenylphosphine.

Among the formula (1) compounds of the present invention, those compounds (1d) in which X is a sulfur atom, are derived using the below-described scheme from the compound (2').

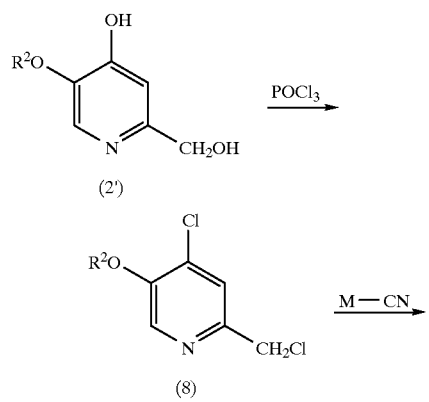

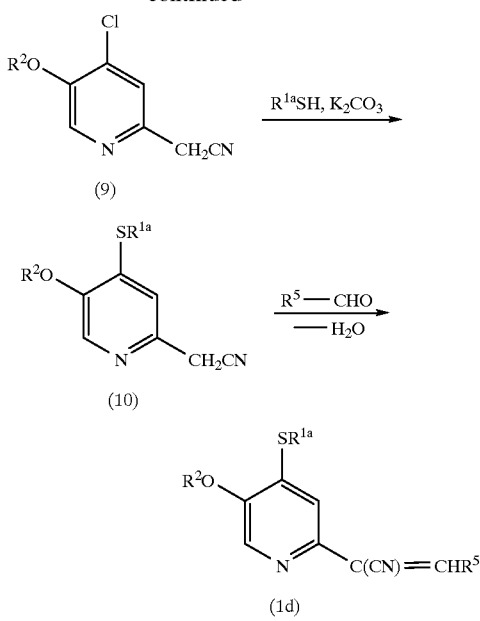

wherein $R^{1a}$, $R^2$, and $R^5$ have the same meanings as described above, and M represents an alkali metal.

The compound (2') is first transformed to a dichloro compound (8), then to an acetonitrile compound (9) through reaction with M-CN, and after being introduced with an $R^{1a}S$ group to a key intermediate (10). The thus-obtained compound (10) is easily derived to compound (1d) of the present invention through a condensation reaction with $R^5$-CHO.

The reactions for obtaining the compound (9) from the compound (8) and obtaining the compound (1d) of the present invention from the key intermediate (10) proceed under conditions same as those described above. The reaction for obtaining a dichloro compound (8) from the compound (2') is carried out through reflux with heat in phosphorus oxychloride. Particularly, the reaction for obtaining the key intermediate (10) from the compound (9) is preferably carried out in a solvent such as alcohol, tetrahydrofuran, dimethylformamide, or dimethyl sulfoxide, in the presence of a base such as potassium carbonate or sodium carbonate in a temperature range from room temperature to 80° C.

When the compound (2) or (2') is replaced by a 6-alkoxy-5-hydroxy-3-pyridinemethanol ($Q^3$=N) or 5-alkoxy-6-hydroxy-2-picoline ($Q^2$=N), a compound of formula (1) in which $Q^2$ or $Q^3$ is a nitrogen atom can be prepared.

In the above reactions, separation of compound (1) of the present invention from reaction mixtures is carried out using a customary method, e.g., extraction with a solvent, recrystalization, or column chromatography.

The thus-obtained compound of the present invention exhibits selective and strong PDE IV inhibitory action and inhibitory action against the production of TNF-α. Therefore, the compound is useful as a PDE IV inhibitor and a TNF-α-production inhibitor, and also as a drug led by one for the prevention and treatment of diseases involving PDE IV and/or TNF-α. The drug of the present invention is useful as a therapeutic agent for the prevention and treatment of immediate or delayed asthma, allergies such as airway-hypersensitive allergy and other allergies stemming from the inhibition of activation of inflammatory blood cells such as eosinocytes, autoimmune diseases such as atopy and rheumatism, depression associated with disturbed metabolism of the cerebrum, cerebral infarction, senile dementia, and memory disorders associated with Parkinson's disease, as well as for osteoporosis, type I and type II diabetes, inflammations, cancers, infections with HIV, AIDS, and shock caused by intracellular toxins.

The compounds of the present invention may be processed into drugs having a variety of forms, including tablets, granules, powders, capsules, inhalants, suspensions, injections, suppositories, and external preparations. When solid preparations are formed, the compound of the present invention is preferably mixed with a vehicle and if necessary with a binder, a disintegrant, an extender, a coating agent, an agent for sugar-coating, etc., and is subsequently formed into tablets, granules, capsules, suppositories, etc. When injections are prepared, the compound of the present invention is dissolved, dispersed, or emulsified in an aqueous carrier for injections in advance, or alternatively the compound is dissolved or dispersed, or suspended upon use of the compound. Injection preparations may be used by way of intravenous administration, arterial administration, intra-peritoneal administration, subcutaneous administration, or dripping.

When the compounds of the present invention are used as preventive or therapeutic drugs for the aforementioned diseases, their doses, which may differ in accordance with the manner of administration and the age, body weight, and conditions of the patient, are preferably 5–100 mg/day in the case of oral administration to an adult.

EXAMPLES

The present invention will next be described by way of examples, which should not be construed as limiting the invention thereto.

Preparation Example 1

Synthesis of 4-substituted-5-alkoxy-2-pyridinemethanols (5) (Process 1)

A 5-alkoxy-4-hydroxy-2-pyridinemethanol (2) (100 mmol) was dissolved in dimethylformamide (100 ml). To the solution were added potassium carbonate (150 mmol) and potassium iodide (3 mmol). While the mixture was stirred on a 65° C. oil bath, a halide reagent (bromocyclopentane in the case of preparation of compound (5a)) (130 mmol) was added dropwise over one hour. The mixture was stirred for 6–12 additional hours under the same conditions. After being cooled, the reaction mixture was poured into cold water and extracted with ethyl acetate. The organic layer was sequentially washed with water and saturated brine, dried, and then concentrated under reduced pressure. The residue was purified by recrystallization or silica gel column chromatography, to thereby obtain compounds (5a) through (5g) shown below.

4-Cyclopentyloxy-5-methoxy-2-pyridinemethanol (5a)
$^1$H-NMR(CDCl$_3$) δ: 1.40–2.20(8H, m), 3.90(3H, s), 4.68 (2H, s), 4.70–5.00(1H, m), 5.35(1H, s), 6.82(1H, s), 8.04 (1H, s).

4-Cyclopentyloxy-5-ethoxy-2-pyridinemethanol (5b)
$^1$H-NMR(CDCl$_3$) δ: 1.42(3H, t, J=7.0 Hz), 1.50–2.10(8H, m), 4.09(2H, q, J=7.0 Hz), 4.65(2H, s), 4.70–4.90(1H, m), 6.73(1H, s), 8.05(1H, s).

5-Methoxy-4-phenethyloxy-2-pyridinemethanol (5c)
$^1$H-NMR(CDCl$_3$) δ: 3.18(2H, t, J=7.0 Hz), 3.91(3H, s), 4.26(2H, t, J=7.0 Hz), 4.63(2H, s), 6.75(1H, s), 7.29(5H, s), 8.05(1H, s).

5-Methoxy-4-(3-phenylpropyloxy)-2-pyridinemethanol (5d)

$^1$H-NMR(CDCl$_3$) δ: 2.00–2.40(2H, m), 2.83(2H, t, J=8.0 Hz), 3.75(1H, br), 3.92(3H, s), 4.05(2H, t, J=8.0 Hz), 4.63(2H, s), 6.70(1H, s), 7.24(5H, s), 8.04(1H, s).

4-Butyloxy-5-methoxy-2-pyridinemethanol (5e)

$^1$H-NMR(CDCl$_3$) δ: 0.98(3H, t, J=7.0 Hz), 1.30–2.00(4H, m), 3.91(3H, s), 4.07(2H, t, J=7.0 Hz), 4.66(2H, s), 6.79(1H, s), 8.03(1H, s).

4-(1-Ethylpropyloxy)-5-methoxy-2-pyridinemethanol (5f)

$^1$H-NMR(CDCl$_3$) δ: 0.96(6H, t, J=7.0 Hz), 1.58–2.00(4H, m), 3.90(3H, s), 4.10–4.40(1H,m), 4.65(2H, s), 6.75(1H, s), 8.04(1H, s).

5-Methoxy-4-methoxymethyloxy-2-pyridinemethanol (5g)

$^1$H-NMR(CDCl$_3$) δ: 3.51(3H, s), 3.95(3H, s), 4.66(2H, s), 5.31(2H, s), 7.04(1H, s), 8.11(1H, s).

Preparation Example 2

Synthesis of 4-substituted-5-alkoxy-2-benzyloxymethylpyridines (5')

A 5-alkoxy-2-benzyloxymethyl-4-hydroxypyridine (2) (10 mmol), a secondary alcohol (2-indanol in the case of preparation of compound (5h')) (12.5 mmol), and triphenylphosphine (15 mmol) were dissolved in tetrahydrofuran (300 ml). Diethyl azodicarboxylate (15 mmol) was added dropwise to the solution under stirring at room temperature, and the mixture was stirred for one hour. After addition of water, the reaction mixture was extracted with in chloroform. The organic layer was sequentially washed with water and saturated brine, dried, and then concentrated under reduced pressure. An ether (100 ml) was added to the residue and insoluble substances were removed by filtration. After concentration of the filtrate, the residue was purified by recrystallization or silica gel column chromatography, to thereby obtain compounds (5h') through (5j') shown below.

2-Benzyloxymethyl-4-(2-indanyloxy)-5-methoxypyridine (5h')

$^1$H-NMR(CDCl$_3$) δ: 3.00–3.60(4H, m), 3.83(3H, s), 4.64 (4H, s), 5.10–5.40(1H, m), 7.06(1H, s), 7.10–7.50(9H, m), 8.06(1H, s).

2-Benzyloxymethyl-5-methoxy-4-(exo-2-norbornyloxy)pyridine (5i')

$^1$H-NMR(CDCl$_3$) δ: 1.00–2.65(10H, m), 3.90(3H, s), 4.10–4.40(1H, m), 4.60(4H, s), 6.95(1H, s), 7.36(5H, s), 8.04(1H, s).

2-Benzyloxymethyl-5-methoxy-4-(tetrahydro-3-furanyloxy)pyridine (5j')

$^1$H-NMR(CDCl$_3$) δ: 2.05–2.40(2H, m), 3.80–4.10(4H, m), 3.91(3H, s), 4.60(2H, s), 4.62(2H, s), 4.90–5.10(1H, m), 6.92(1H, s), 7.36(5H, s), 8.08(1H, s).

Preparation Example 3

Synthesis of 4-substituted-5-alkoxy-2-pyridinemethanols (5) (Process 2)

A 4-substituted-5-alkoxy-2-benzyloxymethylpyridine (5') (10 mmol) was dissolved in acetic acid (50 ml). Pd-black (2 g) was added to the solution, which was hydrogenated at room temperature for 2–6 hours. After removal of the catalyst, the filtrate was concentrated under reduced pressure. The residue was fractionated by a chloroform-aqueous saturated sodium hydrogencarbonate solution. The organic layer was dried and concentrated under reduced pressure. The obtained crystalline residue was optionally recrystallized, to thereby obtain compounds (5h) through (5j) shown below.

4-(2-Indanyloxy)-5-methoxy-2-pyridinemethanol (5h)

$^1$H-NMR(CDCl$_3$) δ: 3.00–3.65(4H, m), 3.84(3H, s), 4.69 (2H, s), 5.10–5.40(1H, m), 6.85(1H, s), 7.10–7.40(4H, m), 8.04(1H, s).

5-Methoxy-4-(exo-2-norbornyloxy)-2-pyridinemethanol (5i)

$^1$H-NMR(CDCl$_3$) δ: 1.00–2.00(8H, m), 2.30–2.60(2H, m), 3.90(3H, s), 4.10–4.40(1H, m), 4.65(2H, s), 6.69(1H, s), 8.03(1H, s).

5-Methoxy-4-(tetrahydro-3-furanyloxy)-2-pyridinemethanol (5j)

$^1$H-NMR(CDCl$_3$) δ: 2.10–2.40(2H, m), 3.80–4.20(4H, m), 3.91(3H, s), 4.66(2H, s), 4.90–5.10(1H, m), 6.71(1H, s), 8.07(1H, s).

Preparation Example 4

Synthesis of 4-substituted-5-alkoxy-2-chloromethylpyridines (6)

A 4-substituted-5-alkoxy-2-pyridinemethanol (5) (0.2 mol) was dissolved in dichloromethane (200 ml). Thionyl chloride (0.3 mol) was added dropwise to the solution under stirring at 5° C. The mixture was allowed to react for 30 minutes under the same conditions. The resultant solution was concentrated under reduced pressure and the residue was fractionated by a chloroform-aqueous saturated sodium hydrogencarbonate solution. The organic layer was dried and concentrated under reduced pressure. Obtained crystalline or oily compounds (6a) through (6j) were used for the subsequent reaction without additional purification.

2-Chloromethyl-4-cyclopentyloxy-5-methoxypyridine (6a)

$^1$H-NMR(CDCl$_3$) δ: 1.40–2.10(8H, m), 3.90(3H, s), 4.60 (2H, s), 4.75–4.97(1H, m), 6.96(1H, s), 8.07(1H, s),

2-Chloromethyl-4-cyclopentyloxy-5-ethoxypyridine (6b)

$^1$H-NMR(CDCl$_3$) δ: 1.40(3H, t, J=7.0 Hz). 1.60–2.10(8H, m), 4.11(2H, q, J=7.0 Hz), 4.59(2H, s), 4.70–4.90(1H, m), 6.95(1H, s), 8.05(1H, s).

2-Chloromethyl-5-methoxy-4-phenethyloxypyridine (6c)

$^1$H-NMR(CDCl$_3$) δ: 3.18(2H, t, J=7.0 Hz), 3.92(3H, s), 4.27(2H, t, J=7.0 Hz), 4.57(2H, s), 6.94(1H, s), 7.30(5H, s), 8.06(1H, s).

2-Chloromethyl-5-methoxy-4-(3-phenylpropyloxy)pyridine (6d)

$^1$H-NMR(CDCl$_3$) δ: 2.00–2.40(2H, m), 2.83(2H, t, J=8.0 Hz), 3.93(3H, s), 4.07(2H, t, J=8.0 Hz), 4.57(2H, s), 6.88 (1H, s), 7.24(5H, s), 8.06(1H, s).

4-Butyloxy-2-chloromethyl-5-methoxypyridine (6e)

$^1$H-NMR(CDCl$_3$) δ: 0.99(3H, t, J=7.0 Hz). 1.30–2.00(4H, m), 3.93(3H, s), 4.09(2H, t, J=7.0 Hz), 4.60(2H, s), 6.97(1H, s), 8.06(1H, s).

2-Chloromethyl-4-(1-ethylpropyloxy)-5-methoxypyridine (6f)

$^1$H-NMR(CDCl$_3$) δ: 0.98(6H, t, J=7.0 Hz), 1.58–2.00(4H, m), 3.92(3H, s), 4.10–4.40(1H, m), 4.60(2H, s) 6.94(1H, s), 8.07(1H, s).

2-Chloromethyl-5-methoxy-4-methoxymethyloxypyridine (6g)

$^1$H-NMR(CDCl$_3$) δ: 3.52(3H, s), 3.96(3H, s), 4.59(2H, s), 5.32(2H, s), 7.23(1H, s), 8.13(1H, s).

2-Chloromethyl-4-(2-indanyloxy)-5-methoxypyridine (6h)

$^1$H-NMR(CDCl$_3$) δ: 3.20(2H, dd, J=4.0, 17.0 Hz), 3.50 (2H, dd, J=6.0, 17.0 Hz), 3.87(3H, s), 4.63(2H, s), 5.15–5.40 (1H, m), 7.04(1H, s), 7.23(4H, s), 8.06(1H, s).

2-Chloromethyl-5-methoxy-4-(exo-2-norbornyloxy)pyridine (6i)

$^1$H-NMR(CDCl$_3$) δ: 1.00–2.10(8H, m). 2.25–2.60(2H, m), 3.91(3H, s), 4.15–4.40(1H, m), 4.60(2H, s), 6.90(1H, s), 8.04(1H, s).

2-Chloromethyl-5-methoxy-4-(tetrahydro-3-furanyloxy)pyridine (6j)

$^1$H-NMR(CDCl$_3$) δ: 2.10–2.40(2H, m), 3.80–4.20(4H, m), 3.92(3H, s), 4.61(2H, s), 4.90–5.10(1H, m), 6.90(1H, s), 8.08(1H, s).

Preparation Example 5

Synthesis of 4-substituted-5-alkoxy-2-pyridineacetonitriles (3)

A 4-substituted-5-alkoxy-2-chloromethylpyridine (6) (0.20 mol) was dissolved in dimethyl sulfoxide (200 ml). Sodium cyanide (0.24 mol) was added to the solution and the mixture was allowed to react at room temperature for 12 hours or at 100° C. for one hour, depending on the reaction rate of the substrate. The reaction mixture was poured into water (500 ml), extracted with ethyl acetate, sequentially washed with water and saturated brine, dried, and then concentrated under reduced pressure. The residue was purified by recrystallization or silica gel column chromatography, to thereby obtain compounds (3a) through (3j) shown below.

4-Cyclopentyloxy-5-methoxy-2-pyridineacetonitrile (3a)

$^1$H-NMR(CDCl$_3$) δ: 1.46–2.20(8H, m), 3.84(2H, s), 3.90 (3H, s), 4.72–5.00(1H, m), 6.90(1H, s), 8.06(1H, s).

4-Cyclopentyloxy-5-ethoxy-2-pyridineacetonitrile (3b)

$^1$H-NMR(CDCl$_3$) δ: 1.42(3H, t, J=7.0 Hz), 1.60–2.20(8H, m), 3.84(2H, s), 4.11(2H, q, J=7.0 Hz), 4.75–5.00(1H, m), 6.88(1H, s), 8.04(1H, s).

5-Methoxy-4-phenethyloxy-2-pyridineacetonitrile (3c)

$^1$H-NMR(CDCl$_3$) δ: 3.18(2H, t, J=7.0 Hz), 3.82(2H, s), 3.92(3H, s), 4.27(2H, t, J=7.0 Hz), 6.86(1H, s), 7.30(5H, s), 8.05(1H, s).

5-Methoxy-4-(3-phenylpropyloxy)-2-pyridineacetonitrile (3d)

$^1$H-NMR(CDCl$_3$) δ: 2.00–2.40(2H, m), 2.84(2H, t, J=8.0 Hz), 3.82(2H, s), 3.94(3H, s), 4.08(2H, t, J=8.0 Hz), 6.81 (1H, s), 7.25(5H, s), 8.06(1H, s).

4-Butyloxy-5-methoxy-2-pyridineacetonitrile (3e)

$^1$H-NMR(CDCl$_3$) δ: 0.99(3H, t, J=7.0 Hz), 1.35–2.10(4H, m), 3.86(2H, s), 3.93(3H, s), 4.09(2H, t, J=7.0 Hz), 6.90(1H, s), 8.05(1H, s).

4-(1-Ethylpropyloxy)-5-methoxy-2-pyridineacetonitrile (3f)

$^1$H-NMR(CDCl$_3$) δ: 0.98(6H, t, J=7.0 Hz), 1.60–2.00(4H, m), 3.85(2H, s), 3.92(3H, s), 4.10–4.40(1H, m), 6.88(1H, s), 8.06(1H, s).

5-Methoxy-4-methoxymethyloxy-2-pyridineacetonitrile (3g)

$^1$H-NMR(CDCl$_3$) δ: 3.52(3H, s), 3.84(2H, s), 3.96(3H, s), 5.32(2H, s), 7.14(1H, s), 8.13(1H, s).

4-(2-Indanyloxy)-5-methoxy-2-pyridineacetonitrile (3h)

$^1$H-NMR(CDCl$_3$) δ: 3.22(2H, dd, J=4.0, 17.0 Hz), 3.51 (2H, dd, J=6.0, 17.0 Hz), 3.86(3H, s), 3.88(2H, s), 5.10–5.40 (1H, m), 6.97(1H, s), 7.23(4H, s), 8.05(1H, s).

5-Methoxy-4-(exo-2-norbornyloxy)n-2-pyridineacetonitrile (3i)

$^1$H-NMR(CDCl$_3$) δ: 1.10–2.00(8H, m), 2.30–2.70(2H, m) 3.85(2H, s), 3.90(3H, s), 4.15–4.40(1H, m), 6.84(1H, s), 8.03(1H, s).

5-Methoxy-4-(tetrahydro-3-furanyloxy)-2-pyridineacetonitrile (3j)

$^1$H-NMR(CDCl$_3$) δ: 2.10–2.50(2H, m), 3.80–4.20(4H, m), 3.86(2H, s), 3.92(3H, s), 4.90–5.20(1H, m), 7.28(1H, s), 8.08(1H, s).

Preparation Example 6

Synthesis of methyl 4-cyclopentyloxy-5-methoxy-2-pyridineacetate (3k)

A HCl-saturated methanol solution (30 ml) was added to 4-cylopentyloxy-5-methoxy-2-pyridineacetonitrile (3a) (2.32 g, 10 mmol) and the solution was refluxed for 30 minutes. The reaction mixture was evaporated to dryness. The residue was dissolved in chloroform and the solution was sequentially washed with aqueous saturated sodium hydrogencarbonate solution and saturated brine, then dried, and then concentrated under reduced pressure, to thereby obtain the title compound (2.36 g, yield 89%).

$^1$H-NMR(CDCl$_3$) δ: 1.60–2.10(8H, m), 3.72(3H, s), 3.76 (2H, s), 3.89(3H, s), 4.70–4.90(1H, m), 6.81(1H, s), 8.04 (1H, s).

Preparation Example 7

Synthesis of 3,5-dichloro-4-pyridinecarbaldehyde

Under an argon atmosphere, to a solution of diisopropylamine (33.6 ml, 0.24 mol) in tetrahydrofuran (400 ml) at −65° C. was added a 1.6 M solution of n-butyl lithium in hexanes (156 ml). After 20 minutes later, a solution of 3,5-dichloropyridine (29.6 g, 0.20 mol) in tetrahydrofuran (150 ml) was added dropwise, and the mixture was stirred for 30 minutes. Subsequently, the mixture was treated with dimethylformamide (23.2 ml, 0.30 mol) in tetrahydrofuran (50 ml), and then stirred for one hour under the same conditions. The reaction mixture was poured into a 5% aqueous ammonium chloride solution (1,000 ml) and extracted with ethyl acetate. The organic layer was sequentially washed with water and saturated brine, dried, and then concentrated under reduced pressure. The residue was chromatographed on silica gel, to thereby obtain the title compound (27.2 g, yield 77%).

$^1$H-NMR(CDCl$_3$) δ: 8.63(2H, s), 10.44(1H, s).

Preparation Example 8

Synthesis of 3,5-dimethoxy-4-pyridinecarbaldehyde

In a similar manner to that in Preparation Example 7, the title compound was prepared.

$^1$H-NMR(CDCl$_3$) δ: 4.02(6H, s), 8.17(2H, s), 10.50(1H, s).

Preparation Example 9

Synthesis of 5-alkoxy-4-chloro-2-chloromethylpyridines (8)

Phosphorus oxychloride (10 ml) was added to a 5-alkoxy-4-hydroxy-2-pyridinemethanol (10 mmol) and the solution was refluxed for three hours. The reaction mixture was concentrated under reduced pressure and the residue was fractionated with a chloroform-aqueous saturated sodium hydrogencarbonate solution. The obtained organic layer was dried and then concentrated under reduced pressure. An obtained crystalline compound (8a) described below was used for the subsequent reaction without additional purification.

4-Chloro-2-chloromethyl-5-methoxypyridine (8a)

$^1$H-NMR(CDCl$_3$) δ: 4.00(3H, s), 4.60(2H, s), 7.50(1H, s), 8.25(1H, s).

Preparation Example 10

Synthesis of 5-alkoxy-4-chloro-2-pyridineacetonitrile (9)

The procedure of Preparation Example 5 was repeated through use of 5-alkoxy-4-chloro-2-chloromethylpyridine (8) and sodium cyanide, to thereby obtain a compound (9a) shown below.

4-chloro-5-methoxy-2-pyridineacetonitrile (9a)

$^1$H-NMR(CDCl$_3$) δ: 3.87(2H, s), 4.01(3H, s), 7.44(1H, s), 8.23(1H, s).

Preparation Example 11

Synthesis of 4-substituted-thio-5-alkoxy-2-pyridineacetonitriles (10)

A 5-alkoxy-4-chloro-2-pyridineacetonitrile (9) (4.5 mmol) was dissolved in dimethylformamide (9 ml). To the solution were added potassium carbonate (5.4 mmol) and R$^{1a}$SH (cyclopentanethiol in the case of preparation of compound (10a)) (5.2 mmol) and the mixture was stirred on a 60° C. oil bath for 3–12 hours. After being cooled, the reaction mixture was poured into cold water and extracted with ethyl acetate. The organic layer was sequentially washed with water and saturated brine, dried, and then concentrated under reduced pressure. The residue was purified by recrystallization or silica gel column chromatography, to thereby obtain a compound (10a) shown below.

4-Cyclopentylthio-5-methoxy-2-pyridineacetonitrile (10a)

$^1$H-NMR(CDCl$_3$) δ: 1.55–2.40(8H, m), 3.55–3.80(1H, m) 3.87(2H, s), 3.97(3H, s), 7.20(1H, s), 7.99(1H, s).

Preparation Example 12

Synthesis of 3-fluoro-4-pyridinecarbaldehyde

The procedure of Preparation Example 7 was repeated to thereby obtain the title compound.

$^1$H-NMR(CDCl$_3$) δ: 7.71(1H, t, J=5.0 Hz), 8.65(1H, d, J=5.0 Hz), 8.73(1H, d, J=1.0 Hz). 10.45(1H, s).

Preparation Example 13

Synthesis of 3,5-dichloro-4-pyridinecarbaldehyde N-oxide

To a benzene solution (100 ml) of 3,5-dichloro-4-pyridinecarbaldehyde (Preparation Example 7) (5.00 g, 28.4 mmol) were added ethylene glycol (10 ml) and p-toluenesulfonic acid hydrate (0.19 g, 1.0 mmol). The mixture, placed in a reaction vessel equipped with a Dean-Stark water separator, was refluxed for eight hours. After being cooled, the reaction mixture was washed with water, dried, and then concentrated under reduced pressure, to thereby obtain the corresponding acetal compound (6.19 g, yield 99%).

$^1$H-NMR(CDCl$_3$) δ: 3.95–4.22(4H, m), 6.38(1H, s), 8.49 (2H, s).

The above-described acetal compound (5.50 g, 25 mmol) was dissolved in dichloromethane (50 ml). To the solution was added 85% m-chloroperbenzoic acid (6.10 g, 30 mmol), and the mixture was stirred at room temperature for 15 hours. The reaction mixture was washed with an aqueous saturated sodium hydrogencarbonate solution, dried, and then concentrated under reduced pressure. The residue was purified by silica gel column chromatography, to thereby obtain the corresponding N-oxide compound (5.24 g, yield 89%).

$^1$H-NMR(CDCl$_3$) δ: 3.95–4.22(4H, m), 6.28(1H, s), 8.15 (2H, s).

The above-described N-oxide compound (4.72 g, 20 mmol) was dissolved in acetone (40 ml)-H$_2$O (10 ml) solution. To the solution was added p-toluenesulfonic acid hydrate (3.80 g, 20 mmol) . The mixture was refluxed for two hours. The reaction mixture was evaporated to dryness. An aqueous saturated sodium hydrogencarbonate solution was added to the residue, which was then extracted with chloroform. The organic layer was washed, dried, and then concentrated under reduced pressure. The residue was purified by silica gel column chromatography, to thereby obtain 3,5-dichloro-4-pyridinecarbaldehyde N-oxide (3.78 g, yield 98%).

$^1$H-NMR(CDCl$_3$) δ: 8.19(2H, s), 10.35(1H, s).

Preparation Example 14

Synthesis of 4-(2-indanyloxy)-5-methoxy-2-pyridinecarbaldehyde

To a dimethyl sulfoxide solution (20 ml) of 4-(2-indanyloxy)-5-methoxy-2-pyridinemethanol (5h) (2.71 g, 10 mmol) and triethylamine (3.03 g, 30 mmol) was added sulfur trioxide-pyridine complex (4.77 g, 30 mmol), and the mixture was stirred at room temperature for 7 hours. The reaction mixture was poured into cold water to cause precipitation of crude crystals. The crude crystals were collected by filtration, dried, and purified by silica gel column chromatography, to thereby obtain the title compound (1.95 g, yield 72%).

$^1$H-NMR(CDCl$_3$) δ: 3.10–3.70(4H, m), 3.96(3H, s), 5.20–5.42(1H, m), 7.23(4H, s), 7.55(1H, s), 8.27(1H, s), 9.95(1H, s).

Preparation Example 15

Synthesis of N-hydroxyethyl-2-pyridone

2-Pyridone (4.76 g, 50 mmol) and ethyl bromoacetate (10.02 g, 60 mmol) were dissolved in acetone (100 ml). Potassium carbonate (8.28 g, 60 mmol) was added to the solution and the mixture was refluxed for two hours with stirring. After being cooled, insoluble substances were removed by filtration and the filtrate was evaporated to dryness. The residue was purified by silica gel column chromatography, to thereby obtain N-ethoxycarbonylmethyl-2-pyridone (7.60 g, yield 84%).

¹H-NMR(CDCl₃) δ: 1.29(3H, t, J=7.0 Hz), 4.24(2H, q, J=7.0 Hz), 4.64(2H, s), 6.10–6.30(1H, m), 6.60(1H, d, J=9.0 Hz), 7.15–7.42(2H, m).

In 100 ml of dioxane, was dissolved N-ethoxycarbonylmethyl-2-pyridone (3.62 g, 20 mmol). To the solution was added 90% LiBH₄ (0.96 g, 40 mmol) and the mixture was refluxed for 20 minutes. Subsequently, ethyl acetate (20 ml) was added to the mixture and the refluxing was carried out for five minutes. The reaction mixture was evaporated to dryness and water was added to the residue. The aqueous solution was extracted with chloroform (three times), dried, and then concentrated under reduced pressure. The residue was purified by silica gel column chromatography, to thereby obtain the title compound (1.15 g, yield 41%).

¹H-NMR(CDCl₃) δ: 3.80–4.30(5H, m), 6.10–6.62(2H, m), 7.20–7.50(2H, m).

Preparation Example 16

Synthesis of 5-cyclopentyloxy-6-methoxy-3-pyridine Acetonitrile

The procedure of Preparation Example 1 was repeated through use of 5-hydroxy-6-methoxy-3-pyridinemethanol and bromocyclopentane, to thereby obtain 5-cyclopentyloxy-6-methoxy-3-pyridinemethanol.

¹H-NMR(CDCl₃) δ: 1.50–2.20(8H, m), 3.98(3H, s), 4.60 (2H, s), 4.73(1H, m), 7.10(1H, d, J=2.0 Hz), 7.63(1H, d, J=2.0 Hz).

The procedure of Preparation Example 4 was repeated through use of 5-cyclopentyloxy-6-methoxy-3-pyridinemethanol and thionyl chloride, to thereby obtain 3-chloromethyl-5-cyclopentyloxy-6-methoxypyridine.

¹H-NMR(CDCl₃) δ: 1.50–2.10(8H, m), 3.93(3H, s), 4.54 (2H, s), 4.70(1H, m), 7.06(1H, d, J=2.0 Hz), 7.67(1H, d, J=2.0 Hz).

The procedure of Preparation Example 5 was repeated through use of 3-chloromethyl-5-cyclopentyloxy-6-methoxypyridine and sodium cyanide, to thereby obtain 5-cyclopentyloxy-6-methoxy-3-pyridineacetonitrile.

¹H-NMR(CDCl₃) δ: 1.50–2.20(8H, m), 3.67(2H, s), 3.98 (3H, s), 4.75(1H, m), 6.99(1H, d. J=2.0 Hz), 7.61(1H, d, J=2.0 Hz).

Preparation Example 17

Synthesis of 6-cyclopentyloxy-5-methoxy-2-pyridineacetonitrile

The procedure of Preparation Example 1 was repeated through use of 6-hydroxy-5-methoxy-2-picoline and bromocyclopentane, to thereby obtain 6-cyclopentyloxy-5-methoxy-2-picoline.

¹H-NMR(CDCl₃) δ: 1.58–2.03(8H, m), 2.36(3H, s), 3.80 (3H, s), 5.44(1H, m), 6.59(1H, d, J=8.0 Hz), 6.92(1H, d, J=8.0 Hz).

6-Cyclopentyloxy-5-methoxy-2-picoline (0.83 g, 4.0 mmol) and N-bromosuccinimide (0.80 g, 4.4 mmol) were dissolved in carbon tetrachloride (10 ml). The solution in which benzoyl peroxide was added in a catalytic amount was refluxed for two hours. After being cooled, water was added to the reaction mixture, which was extracted with ethyl acetate. The organic layer was washed with water, dried, and then concentrated under reduced pressure, to thereby obtain a residue which was used for the subsequent reaction.

The procedure of Preparation Example 5 was repeated through use of the above-described residue and sodium cyanide, to thereby obtain 6-cyclopentyloxy-5-methoxy-2-pyridineacetonitrile (0.72 g, yield 77%).

¹H-NMR(CDCl₃) δ: 1.50–2.40(8H, m), 3.73(2H, s), 3.84 (3H, s), 5.40(1H, m), 6.80(1H, d, J=8.0 Hz), 7.00(1H, d, J=8.0 Hz).

Preparation Example 18

Synthesis of 5-methoxy-4-[2-(4-methyl-5-thiazolyl) ethyloxy]-2-pyridineacetonitrile The procedure of Preparation Example 1 was repeated through use of 4-hydroxy-5-methoxy-2-pyridinemethanol and 5-(2-chloroethyl)-4-methylthiazole, to thereby obtain 5-methoxy-4-[2-(4-methyl-5-thiazolyl)ethyloxy]-2-pyridinemethanol.

¹H-NMR(CDCl₃) δ: 2.46(3H, s), 3.33(2H, t, J=6.5 Hz), 3.92(3H, s), 4.22(2H, t, J=6.5 Hz), 4.65(2H, s), 6.75(1H, s), 8.07(1H, s), 8.62(1H, s).

The procedure of Preparation Example 4 was repeated through use of 5-methoxy-4-[2-(4-methyl-5-thiazolyl) ethyloxy]-2-pyridinemethanol and thionyl chloride, to thereby obtain 2-chloromethyl-5-methoxy-4-[2-(4-methyl-5-thiazolyl)ethyloxy]pyridine.

¹H-NMR(CDCl₃) δ: 2.47(3H, s), 3.34(2H, t, J=6.5 Hz), 3.94(3H, s), 4.25(2H, t. J=6.5 Hz), 4.59(2H, s), 6.94(1H, s), 8.08(1H, s), 8.61(1H, s).

The procedure of Preparation Example 5 was repeated through use of 2-chloromethyl-5-methoxy-4-[2-(4-methyl-5-thiazolyl)ethyloxy]pyridine and sodium cyanide, to thereby obtain 5-methoxy-4-[2-(4-methyl-5-thiazolyl) ethyloxy]-2-pyridineacetonitrile.

¹H-NMR(CDCl₃) δ: 2.47(3H, s), 3.35(2H, t, J=6.5 Hz), 3.85(2H, s), 3.93(3H, s), 4.24(2H, t, J=6.5 Hz ), 6.87(1H, s), 8.07(1H, s), 8.62(1H, s).

Example 1

Synthesis of (Z)-2-(4-cyclopentyloxy-5-methoxy-2-pyridyl)-3-(3,5-dichloro-4-pyridyl)propenenitrile (formula (1), wherein $R^1$=cyclopentyl, $R^2$=CH₃, $R^3$=CN, $R^4$=H, $R^5$=3,5-dichloro-4-pyridyl, and X=O):

4-Cyclopentyloxy-5-methoxy-2-pyridineacetonitrile (3a) (16.24 g, 70 mmol) and 3,5-dichloro-4-pyridinecarbaldehyde (Preparation Example 7) (12.94 g, 73.5 mmol) were dissolved in methanol (180 ml). While the solution was stirred at 5° C., a CH₃ONa-CH₃OH solution (1 M, 77 ml) was added dropwise. The mixture was stirred for 30 additional minutes under the same conditions. Precipitated crystals were collected by filtration and recrystallized from ethanol, to thereby obtain the title compound (24.83 g, yield 91%).

Melting point: 126°–126.5° C.

¹H-NMR(CDCl₃) δ: 1.60–2.15(8H, m), 3.98(3H, s), 4.92–4.98(1H, m), 7.26(1H, s), 8.19(1H, s), 8.20(1H, s), 8.61(2H, s).

Example 2

The procedure of Example 1 was repeated through use of 4-cyclopentyloxy-5-methoxy-2-pyridineacetonitrile (3a) and 2,6-dichlorobenzaldehyde, to thereby obtain the compound shown below.

(Z)-2-(4-Cyclopentyloxy-5-methoxy-2-pyridyl)-3-(2,6-dichlorophenyl)propenenitrile (formula (1), wherein $R^1$=cyclopentyl, $R^2$=$CH_3$, $R^3$=CN, $R^4$=H, $R^5$=2,6-dichlorophenyl, and X=O)

Melting point: 129–130° C.

$^1$H-NMR(CDCl$_3$) δ: 1.60–2.20(8H, m), 3.97(3H, s), 4.92–4.98(1H, m), 7.25(1H, s), 7.26–7.31(1H, m), 7.42(2H, d, J=7.0 Hz), 8.20(1H, s), 8.23(1H, s).

Example 3

The procedure of Example 1 was repeated through use of 4-cyclopentyloxy-5-methoxy-2-pyridineacetonitrile (3a) and 3-pyridinecarbaldehyde, to thereby obtain the compound shown below.

(Z)-2-(4-Cyclopentyloxy-5-methoxy-2-pyridyl)-3-(3-pyridyl)propenenitrile (formula (1), wherein $R^1$=cyclopentyl, $R^2$=$CH_3$, $R^3$=CN, $R^4$=H, $R^5$=3-pyridyl, and X=O)

Melting point: 122.5–123.5° C.

$^1$H-NMR(CDCl$_3$) δ:1.50–2.20(8H, m), 3.98(3H, s), 4.84–5.06(1H, m), 7.30(1H, s), 7.48(1H, dd, J=5.0, 8.0 Hz), 8.20(1H, s), 8.38(1H, s), 8.55(1H, dt, J=2.0, 8.0 Hz), 8.70 (1H, dd, J=2.0, 5.0 Hz), 8.98(1H, d, J=2.0 Hz).

Example 4

The procedure of Example 1 was repeated through use of 4-cyclopentyloxy-5-methoxy-2-pyridineacetonitrile (3a) and 4-pyridinecarbaldehyde, to thereby obtain the compound shown below.

(Z)-2-(4-Cyclopentyloxy-5-methoxy-2-pyridyl)-3-(4-pyridyl)propenenitrile (formula (1), wherein $R^1$=cyclopentyl, $R^2$=$CH_3$, $R^3$=CN, $R^4$=H, $R^5$=4-pyridyl, and X=O)

Melting point: 142–142.5° C.

$^1$H-NMR(CDCl$_3$) δ: 1.64–2.14(8H, m), 3.97(3H, s), 4.92–4.98(1H, m), 7.28(1H, s), 7.74(2H, dd, J=2.0, 6.0 Hz), 8.16(1H, s), 8.26(1H, s), 8.74(2H, dd, J=2.0, 6.0 Hz).

Example 5

The procedure of Example 1 was repeated through use of 4-cyclopentyloxy-5-methoxy-2-pyridineacetonitrile (3a) and 2-methoxy-1-naphthaldehyde, to thereby obtain the compound shown below.

(Z)-2-(4-Cyclopentyloxy-5-methoxy-2-pyridyl)-3-(2-methoxy-1-naphthyl)propenenitrile (formula (1), wherein $R^1$=cyclopentyl, $R^2$=$CH_3$, $R^3$=CN, $R^4$=H, $R^5$=2-methoxy-1-naphthyl, and X=O)

Melting point: 168–169° C.

$^1$H-NMR(CDCl$_3$) δ: 1.60–2.15(8H, m), 3.97(3H, s), 4.04 (3H, s), 4.80–5.00(1H, m), 7.29(1H, s), 7.34–7.42(2H, m), 7.48–7.53(1H, m), 7.80–7.93(3H, m), 8.21(1H, s), 8.69(1H, s).

Example 6

The procedure of Example 1 was repeated through use of 4-cyclopentyloxy-5-methoxy-2-pyridineacetonitrile (3a) and 2-chlorobenzaldehyde, to thereby obtain the compound shown below.

(Z)-3-(2-chlorophenyl)-2-(4-cyclopentyloxy-5-methoxy-2-pyridyl)propenenitrile (formula (1), wherein $R^1$=cyclopentyl, $R^2$=$CH_3$, $R^3$=CN, $R^4$=H, $R^5$=2-chlorophenyl, and X=O)

Melting point: 122–123° C.

$^1$H-NMR(CDCl$_3$) δ: 1.60–2.15(8H, m), 3.96(3H, s), 4.92–4.97(1H, m), 7.26(1H, s), 7.35–7.41(2H, m), 7.46–7.50(1H, m), 8.10–8.18(1H, m), 8.19(1H, s), 8.63(1H, s).

Example 7

The procedure of Example 1 was repeated through use of 4-cyclopentyloxy-5-methoxy-2-pyridineacetonitrile (3a) and 4-cyanobenzaldehyde, to thereby obtain the compound shown below.

(Z)-3-(4-cyanophenyl)-2-(4-cyclopentyloxy-5-methoxy-2-pyridyl)propenenitrile (formula (1), wherein $R^1$=cyclopentyl, $R^2$=$CH_3$, $R^3$=CN, $R^4$=H, $R^5$=4-cyanophenyl, and X=O)

Melting point: 149–150° C.

$^1$H-NMR(CDCl$_3$) δ: 1.55–2.20(8H, m), 3.97(3H, s), 4.80–5.10(1H, m), 7.28(1H, s), 7.75(2H, d, J=9.0 Hz), 8.03(2H, d, J=9.0 Hz), 8.15(1H, s), 8.33(1H, s).

Example 8

The procedure of Example 1 was repeated through use of 4-cyclopentyloxy-5-methoxy-2-pyridineacetonitrile (3a) and 4-trifluoromethylbenzaldehyde, to thereby obtain the compound shown below.

(Z)-2-(4-Cyclopentyloxy-5-methoxy-2-pyridyl)-3-(4-trifluoromethylphenyl)propeneitrile (formula (1), wherein $R^1$=cyclopentyl, $R^2$=$CH_3$, $R^3$=CN, $R^4$=H, $R^5$=4-trifluoromethylphenyl, and X=O)

Melting point: 116–117° C.

$^1$H-NMR(CDCl$_3$) δ: 1.55–2.20(8H, m), 3.97(3H, s), 4.80–5.10(1H, m), 7.27(1H, s), 7.72(2H, d, J=9.0 Hz), 8.04(2H, d, J=9.0 Hz), 8.15(1H, s), 8.35(1H, s).

Example 9

The procedure of Example 1 was repeated through use of 4-cyclopentyloxy-5-methoxy-2-pyridineacetonitrile (3a) and 2,6-dimethoxybenzaldehyde, to thereby obtain the compound shown below.

(Z)-2-(4-Cyclopentyloxy-5-methoxy-2-pyridyl)-3-(2,6-dimethoxyphenyl)propenenitrile (formula (1), wherein $R^1$=cyclopentyl, $R^2$=$CH_3$, $R^3$=CN, $R^4$=H, $R^5$=2,6-dimethoxyphenyl, and X=O)

Melting point: 168–170° C.

$^1$H-NMR(CDCl$_3$) δ: 1.55–2.10(8H, m), 3.89(6H, s), 3.94 (3H, s), 4.80–5.10(1H, m), 6.60(2H d J=8.0 Hz), 7.24(1H, s), 7.42(1H, t, J=8.0 Hz), 8.16(1H, s), 8.27(1H, s).

Example 10

The procedure of Example 1 was repeated through use of 4-cyclopentyloxy-5-methoxy-2-pyridineacetonitrile (3a) and 4-quinolinecarbaldehyde, to thereby obtain the compound shown below.

(Z)-2-(4-Cyclopentyloxy-5-methoxy-2-pyridyl)-3-(4-quinolyl)propenenitrile (formula (1), wherein $R^1$=cyclopentyl, $R^2$=$CH_3$, $R^3$=CN, $R^4$=H, $R^5$=4-quinolyl, and X=O)

Melting point: 160–161° C.

$^1$H-NMR(CDCl$_3$) δ: 1.55–2.10(8H, m), 4.00(3H, s), 4.80–5.10(1H, m), 7.32(1H, s), 7.45–8.30(5H, m), 8.21(1H, s), 9.02(1H, s), 9.04(1H, d, J=4.0 Hz).

Example 11

The procedure of Example 1 was repeated through use of 4-cyclopentyloxy-5-methoxy-2-pyridineacetonitrile (3a) and 3,5-dimethoxy-4-pyridinecarbaldehyde (Preparation Example 8), to thereby obtain the compound shown below.

(Z)-2-(4-Cyclopentyloxy-5-methoxy-2-pyridyl)-3-(3,5-dimethoxy-4-pyridyl)propenenitrile (formula (1), wherein $R^1$=cyclopentyl, $R^2$=CH$_3$, $R^3$=CN, $R^4$=H, $R^5$=3,5-dimethoxy-4-pyridyl, and X=O)

Melting point: 143–144° C.

$^1$H-NMR(CDCl$_3$) δ: 1.55–2.10(8H, m), 3.96(3H, s), 4.00 (6H, s), 4.80–5.10(1H, m), 7.25(1H, s), 8.11(2H, s), 8.17 (2H, s).

Example 12

The procedure of Example 1 was repeated through use of 4-cyclopentyloxy-5-methoxy-2-pyridineacetonitrile (3a) and benzaldehyde, to thereby obtain the compound shown below.

(Z)-2-(4-Cyclopentyloxy-5-methoxy-2-pyridyl)-3-phenylpropenenitrile (formula (1), wherein $R^1$=cyclopentyl, $R^2$=CH$_3$, $R^3$=CN, $R^4$=H, $R^5$=phenyl, and X=O)

Melting point: 107–108° C.

$^1$H-NMR(CDCl$_3$) δ: 1.40–2.30(8H, m), 3.96(3H, s), 4.80–5.10(1H, m), 7.26(1H, s), 7.35–7.60(3H, m), 7.80–8.10(2H, m), 8.15(1H, s), 8.32(1H, s).

Example 13

The procedure of Example 1 was repeated through use of 4-cyclopentyloxy-5-methoxy-2-pyridineacetonitrile (3a) and 2-thiophenecarbaldehyde, to thereby obtain the compound shown below.

(Z)-2-(4-Cyclopentyloxy-5-methoxy-2-pyridyl)-3-(2-thienyl)propenenitrile (formula (1), wherein $R^1$=cyclopentyl, $R^2$=CH$_3$, $R^3$=CN, $R^4$=H, $R^5$=2-thienyl, and X=O)

Melting point: 89–90° C.

$^1$H-NMR(CDCl$_3$) δ: 1.60–2.20(8H, m), 3.95(3H, s), 4.80–5.00 (1H, m), 7.05–7.25(1H, m), 7.19(1H, s), 7.57(1H, d, J=5.0 Hz), 7.72(1H, d, J=4.0 Hz), 8.12(1H, s), 8.44(1H, s).

Example 14

The procedure of Example 1 was repeated through use of 5-methoxy-4-phenethyloxy-2-pyridineacetonitrile (3c) and 3,5-dichloro-4-pyridinecarbaldehyde (Preparation Example 7), to thereby obtain the compound shown below.

(Z)-3-(3,5-Dichloro-4-pyridyl)-2-(5-methoxy-4-phenethyloxy-2-pyridyl)propenenitrile (formula (1), wherein $R^1$=phenethyl, $R^2$=CH$_3$, $R^3$=CN, $R^4$=H, $R^5$=3,5-dichloro-4-pyridyl, and X=O)

Melting point: 141.5–142.5° C.

$^1$H-NMR(CDCl$_3$) δ: 3.21(2H, t, J=8.0 Hz). 4.00(3H, s), 4.34(2H, t, J=8.0 Hz), 7.20–7.40(6H, m), 8.16(1H, s), 8.22 (1H, s), 8.60(2H, s).

Example 15

The procedure of Example 1 was repeated through use of 5-methoxy-4-(3-phenylpropyloxy)-2-pyridineacetonitrile (3d) and 3,5-dichloro-4-pyridinecarbaldehyde (Preparation Example 7), to thereby obtain the compound shown below.

(Z)-3-(3,5-Dichloro-4-pyridyl)-2-[5-methoxy-4-(3-phenylpropyloxy)-2-pyridyl]propenenitrile (formula (1), wherein $R^1$=3-phenylpropyl, $R^2$=CH$_3$, $R^3$=CN, $R^4$=H, $R^5$=3,5-dichloro-4-pyridyl, and X=O)

Melting point: 101–102° C.

$^1$H-NMR(CDCl$_3$) δ: 2.00–2.40(2H, m), 2.86(2H, t, J=8.0 Hz). 4.02(3H, s), 4.15(2H, t, J=8.0 Hz), 7.10–7.40(6H, m), 8.16(1H, s), 8.22(1H, s), 8.60(2H, s).

Example 16

The procedure of Example 1 was repeated through use of 4-butyloxy-5-methoxy-2-pyridineacetonitrile (3e) and 3,5-dichloro-4-pyridinecarbaldehyde (Preparation Example 7), to thereby obtain the compound shown below.

(Z)-2-(4-Butyloxy-5-methoxy-2-pyridyl)-3-(3,5-dichloro-4-pyridyl)propenenitrile (formula (1), wherein $R^1$=butyl, $R^2$=CH$_3$, $R^3$=CN, $R^4$=H, $R^5$=3,5-dichloro-4-pyridyl, and X=O)

Melting point: 108–109° C.

$^1$H-NMR(CDCl$_3$) δ: 1.00(3H, t, J=7.0 Hz), 1.30–2.10(4H, m), 4.00(3H, s), 4.16(2H, t, J=7.0 Hz), 7.27(1H, s), 8.19(1H, s), 8.21(1H, s), 8.61(2H, s).

Example 17

The procedure of Example 1 was repeated through use of 4-(1-ethylpropyloxy)-5-methoxy-2-pyridineacetonitrile (3f) and 3,5-dichloro-4-pyridinecarbaldehyde (Preparation Example 7), to thereby obtain the compound shown below.

(Z)-3-(3,5-Dichloro-4-pyridyl)-2-[4-(1-ethylpropyloxy)-5-methoxy-2-pyridyl]propenenitrile (formula (1), wherein $R^1$=ethylpropyl, $R^2$=CH$_3$, $R^3$=CN, $R^4$=H, $R^5$=3,5-dichloro-4-pyridyl, and X=O)

Melting point: 127–127.5° C.

$^1$H-NMR(CDCl$_3$) δ:1.00(6H, t, J=7.0 Hz). 1.60–2.00(4H, m), 4.00(3H, s), 4.10–4.40(1H, m), 7.25(1H, s), 8.19(1H, s), 8.22(1H, s), 8.61(2H, s).

Example 18

The procedure of Example 1 was repeated through use of 4-cyclopentyloxy-5-ethoxy-2-pyridineacetonitrile (3d) and 3,5-dichloro-4-pyridinecarbaldehyde (Preparation Example 7), to thereby obtain the compound shown below.

(Z)-2-(4-Cyclopentyloxy-5-ethoxy-2-pyridyl)-3-(3,5-dichloro-4-pyridyl)propenenitrile (formula (1), wherein $R^1$=cyclopentyl, $R^2$=C$_2$H$_5$, $R^3$=CN, $R^4$=H, $R^5$=3,5-dichloro-4-pyridyl, and X=O)

Melting point: 90–91° C.

$^1$H-NMR(CDCl$_3$) δ: 1.46(3H, t, J=7.0 Hz), 1.60–2.20(8H, m), 4.19(2H, q, J=7.0 Hz), 4.80–5.00(1H, m), 7.26(1H, s), 8.18(1H, s), 8.19(1H, s), 8.61(2H, s).

Example 19

The procedure of Example 1 was repeated through use of 4-(2-indanyloxy)-5-methoxy-2-pyridineacetonitrile (3h) and 3,5-dichloro-4-pyridinecarbaldehyde (Preparation Example 7), to thereby obtain the compound shown below.

(Z)-3-(3,5-Dichloro-4-pyridyl)-2-[4-(2-indanyloxy)-5-methoxy-2-pyridyl]propenenitrile (formula (1), wherein $R^1$=2-indanyl, $R^2$=CH$_3$, $R^3$=CN, $R^4$=H, $R^5$=3,5-dichloro-4-pyridyl, and X=O)

Melting point: 185–185.5° C.

$^1$-NMR(CDCl$_3$) δ: 3.28(2H, dd, J=3.5, 17.0 Hz), 3.51(2H, dd, J=6.0, 17.0 Hz), 3.92(3H, s), 5.32–5.38(1H, m), 7.17–7.28(5H, m), 8.21(1H, s), 8.22(1H, s), 8.61(2H, s).

Example 20

The procedure of Example 1 was repeated through use of 5-methoxy-4-(tetrahydro-3-furanyloxy)-2-pyridineacetonitrile (3j) and 3,5-dichloro-4-pyridinecarbaldehyde (Preparation Example 7), to thereby obtain the compound shown below.

(Z)-3-(3,5-Dichloro-4-pyridyl)-2-[5-methoxy-4-(tetrahydro-3-furanyloxy)-2-pyridyl]propenenitrile (formula (1), wherein $R^1$=tetrahydro-3-furanyl, $R^2$=CH$_3$, $R^3$=CN, $R^4$=H, $R^5$=3,5-dichloro-4-pyridyl, and X=O)

Melting point: 138–140° C.

$^1$-NMR(CDCl$_3$) δ: 2.10–2.50(2H, m), 3.80–4.20(4H, m), 3.99(3H, s), 5.00–5.20(1H, m),7.20(1H, s), 8.21(1H, s), 8.24(1H, s), 8.61(2H, s).

Example 21

The procedure of Example 1 was repeated through use of 5-methoxy-4-(exo-2-norbornyloxy)-2-pyridineacetonitrile (3i) and 3,5-dichloro-4-pyridinecarbaldehyde (Preparation Example 7), to thereby obtain the compound shown below.

(Z)-3-(3,5-Dichloro-4-pyridyl)-2-[5-methoxy-4-(exo-2-norbornyloxy)-2-pyridyl]propenenitrile (formula (1), wherein R$^1$=exo-2-norbornyl, R=CH$_3$, R$^3$=CN, R$^4$=H, R$^5$=3,5-dichloro-4-pyridyl, and X=O)

Melting point: 145.5–146.5° C.

$^1$-NMR (CDCl$_3$) δ: 1.10–2.00(8H, m),2.30–2.70(2H, m), 3.98(3H, s), 4.30–4.50(1H, m), 7.21(1H, s), 8.19(2H, s) 8.61(2H, s).

Example 22

Synthesis of methyl (E)-2-(4-cyclopentyloxy-5-methoxy-2-pyridyl)-3-(3,5-dichloro-4-pyridyl)propenoate (formula (1), wherein R$^1$=cyclopentyl, R$^2$=CH$_3$, R$^3$=CO$_2$CH$_3$, R$^4$=H, R$^5$=3,5-dichloro-4-pyridyl, and X=O):

Under the same conditions in Example 1 and through use of methyl 4-cyclopentyloxy-5-methoxy-2-pyridineacetate (3k) and 3,5-dichloro-4-pyridinecarbaldehyde (Preparation Example 7) in methanol containing a CH$_3$ONa-CH$_3$OH solution (1 M), the title compound was prepared.

Melting point: 119–120° C.

$^1$-NMR(CDCl$_3$) δ: 1.55–1.90(8H, m), 3.86(3H, s), 3.91 (3H, s), 4.56–4.60(1H, m), 6.70(1H, s), 7.57(1H, s), 7.94 (1H, s), 8.40(2H, s).

Example 23

Synthesis of (Z)-3-(4-cyclopentyloxy-5-methoxy-2-pyridyl)-2-(3-pyridyl)propenenitrile (formula (1), wherein R$^1$=cyclopentyl, R$^2$=CH$_3$, R$^3$=H, R$^4$=CN, R$^5$=3-pyridyl, and X=O):

4-Cyclopentyloxy-5-methoxy-2-pyridinecarbaldehyde (4.42 g, 20 mmol) and 3-pyridineacetonitrile (2.36 g, 20 mmol) were dissolved in methanol (60 ml). While the solution was stirred at 5° C., a CH$_3$ONa-CH$_3$OH solution (1 M, 23 ml) was added dropwise. The mixture was stirred for 30 additional minutes under the same condition. The reaction mixture was poured into cold water and extracted with chloroform. The organic layer was dried and then concentrated under reduced pressure. The residue was chromatographed on silica gel, to thereby obtain the title compound (4.54 g, yield 71%) from a 1% (v/v) methanol-chloroform-eluted fraction.

Melting point: 119–119.5° C.

$^1$-NMR(CDCl$_3$) δ: 1.60–2.20(8H, m), 4.00(3H, s), 4.92–4.98(1H, m), 7.41(1H, dd, J=5.0, 7.0 Hz), 7.64(1H, s), 7.72(1H, s), 7.98–8.03(1H, m), 8.26(1H, s), 8.64(1H, dd. J=1.5. 5.0 Hz), 8.97(1H, d, J=2.0 Hz).

Example 24

The procedure of Example 23 was repeated through use of 4-cyclopentyloxy-5-methoxy-2-pyridinecarbaldehyde and 2-thiopheneacetonitrile, to thereby obtain the compound shown below.

(Z)-3-(4-Cyclopentyloxy-5-methoxy-2-pyridyl)-2-(2-thienyl)propenenitrile (formula (1), wherein R$^1$=cyclopentyl, R$^2$=CH$_3$, R$^3$=H, R$^4$=CN, R$^5$=2-thienyl, and X=O), Melting point: 101–102° C.

$^1$-NMR(CDCl$_3$) δ: 1.60–2.15(8H, m), 3.98(3H, s); 4.92–4.98(1H, m), 7.08(1H, dd, J=4.0, 5.0 Hz), 7.33(1H, dd, J=1.0, 5.0 Hz), 7.43(1H, s), 7.44(1H, dd, J=1.0, 4.0 Hz), 7.62(1H, s), 8.22(1H, s).

Example 25

The procedure of Example 23 was repeated through use of 4-cyclopentyloxy-5-methoxy-2-pyridinecarbaldehyde and phenylacetonitrile, to thereby obtain the compound shown below.

(Z)-3-(4-Cyclopentyloxy-5-methoxy-2-pyridyl)-2-phenylpropenenitrile (formula (1), wherein R$^1$=cyclopentyl, R$^2$=CH$_3$, R$^3$=H, R$^4$=CN, R$^5$=phenyl, and X=O), Melting point: 91–91.5° C.

$^1$-NMR(CDCl$_3$) δ: 1.60–2.20(8H, m), 3.99(3H, s), 4.92–4.98(1H, m), 7.38–7.49(3H, m), 7.62(1H, s), 7.70–7.75(2H, m) 7.77(1H, s) 8.23(1H, s).

Example 26

The procedure of Example 1 was repeated through use of 5-methoxy-4-methoxymethyloxy-2-pyridineacetonitrile (3g) and 3,5-dichloro-4-pyridinecarbaldehyde (Preparation Example 7), to thereby obtain the compound shown below.

(Z)-3-(3,5-Dichloro-4-pyridyl)-2-(5-methoxy-4-methoxymethyloxy-2-pyridyl)propenenitrile (formula (1), wherein R$^1$=CH$_2$OCH$_3$, R$^2$=CH$_3$, R$^3$=CN, R$^4$=H, R$^5$=3,5-dichloro-4-pyridyl, and X=O), Melting point: 140–141° C.

$^1$-NMR(CDCl$_3$) δ: 3.54(3H, s), 4.03(3H, s), 5.38(2H, s) 7.54(1H, s), 8.14(1H, s), 8.28(1H, s), 8.61(2H, s).

Example 27

Synthesis of (Z)-3-(3,5-dichloro-4-pyridyl)-2-(4-hydroxy-5-methoxy-2-pyridyl)propenenitrile (formula (1), wherein R$^1$=H, R$^2$=CH$_3$, R$^3$=CN, R$^4$=H, R$^5$=3,5-dichloro-4-pyridyl, and X=O):

In 8 ml of dichloromethane, was dissolved (Z)-3-(3,5-dichloro-4-pyridyl)-2-(5-methoxy-4-methoxymethyloxy-2-pyridyl)propenenitrile (formula (1), wherein R$^1$=CH$_2$OCH$_3$, R$^2$=CH$_3$, R$^3$=CN, R$^4$=H, R$^5$=3,5-dichloro-4-pyridyl, and X=O) (0.73 g, 2 mmol) . While the solution was stirred at 0° C., trifluoroacetic acid (2 ml) was added. The mixture was stirred for additional two hours. The reaction mixture was evaporated to dryness. The residue was dissolved through addition of water, and the pH of the solution was adjusted to about 6 through addition of an aqueous saturated sodium hydrogencarbonate solution. Precipitated crystals were collected by filtration, washed with water, and recrystallized from ethanol, to thereby obtain the title compound (0.56 g, yield 88%), Melting point: 218–219.5° C.

$^1$-NMR(DMSO-d$_6$) δ: 3.94(3H, s), 7.33(1H, s), 8.19(1H, s), 8.29(1H, s), 8.81(2H, s).

Example 28

Synthesis of (Z)-3-(3,5-dichloro-4-pyridyl)-2-[4-(3-hydroxypropyloxy)-5-methoxy-2-pyridyl]propenenitrile (formula (1), wherein R$^1$=(CH$_2$)$_3$OH, R$^2$=CH$_3$, R$^3$=CN, R$^4$=H, R$^5$=3,5-dichloro-4-pyridyl, and X=O):

In 4 ml of dimethylformamide, was dissolved (Z)-3-(3, 5-dichloro-4-pyridyl)-2-(4-hydroxy-5-methoxy-2-pyridyl) propenenitrile (formula (1), wherein R$^1$=H, R$^2$=CH$_3$, $R^3$=CN, $R^4$=H, $R^5$=3,5-dichloro-4-pyridyl, and X=O) (400 mg, 1.24 mmol), To the solution were added 3-bromopropanol (0.132 ml, 1.48 mmol) and potassium carbonate (204 mg, 1.48 mmol). The mixture was stirred on a 60° C. oil bath for three hours. After being cooled, the reaction mixture was poured into cold water and extracted with in ethyl acetate. The organic layer was sequentially washed with water and saturated brine, dried, and then concentrated under reduced pressure. The residue was purified by silica gel column chromatography. Crystals obtained from the 1% hexane-ethyl acetate (1:1)-eluted fraction were recrystallized from hexane-diethyl ether, to thereby obtain the title compound (360 mg, yield 76%).

Melting point: 111–113° C.

$^1$-NMR(CDCl$_3$) δ: 1.94(1H, t, J=5.0 Hz), 2.12–2.20(2H, m), 3.87–3.92(2H, m), 4.00(3H, s), 4.33(2H, t, J=6.0 Hz), 7.30(1H, s), 8.18(1H, s), 8.22(1H, s), 8.61(2H, s).

Example 29

The procedure of Example 1 was repeated through use of 4-cyclopentylthio-5-methoxy-2-pyridineacetonitrile (10a) and 3,5-dichloro-4-pyridinecarbaldehyde (Preparation Example 7), to thereby obtain the compound shown below.

(Z)-2-(4-Cyclopentylthio-5-methoxy-2-pyridyl)-3-(3,5-dichloro-4-pyridyl)propenenitrile (formula (1), wherein $R^1$=cyclopentyl, $R^2$=CH$_3$, $R^3$=CN, $R^4$=H, $R^5$=3,5-dichloro-4-pyridyl, and X=S).

Melting point: 147–148° C.

$^1$H-NMR(CDCl$_3$) δ: 1.50–2.40(8H, m)), 3.60–3.95(1H, m), 4.04(3H, s), 7.59(1H, s), 8.14(1H, s), 8.18(1H, s), 8.61(2H, s).

Example 30

The procedure of Example 23 was repeated through use of 4-cyclopentyloxy-5-methoxy-2-pyridinecarbaldehyde and 3,5-dichloro-4-pyridineacetonitrile, to thereby obtain the compound shown below.

(Z)-3-(4-Cyclopentyloxy-5-methoxy-2-pyridyl)-2-(3,5-dichloro-4-pyridyl)propenenitrile (formula (1), wherein $R^1$=cyclopentyl, $R^2$=CH$_3$, $R^3$=H, $R^4$=CN, $R^5$=3,5-dichloro-4-pyridyl, and X=O), Melting point: 140.5–142° C.

$^1$-NMR(CDCl$_3$) δ: 1.50–2.00 (8H, m), 3.88(3H, s), 4.50–4.70(1H, m), 6.68(1H, s), 7.51(1H, s), 7.89(1H, s), 8.57(2H, s).

Example 31

Synthesis of (E)-2-(4-cyclopentyloxy-5-methoxy-2-pyridyl)-3-(3,5-dichloro-4-pyridyl)propenoic acid (formula (1), wherein $R^1$=cyclopentyl, $R^2$=CH$_3$, $R^3$=CO$_2$H, $R^4$=H, $R^5$=3,5-dichloro-4-pyridyl, and X=O):

Methyl (E)-2-(4-cyclopentyloxy-5-methoxy-2-pyridyl)-3-(3,5-dichloro-4-pyridyl)propenoate (formula (1), wherein $R^1$=cyclopentyl, $R^2$=CH$_3$, $R^3$=CO$_2$CH$_3$, $R^4$=H, $R^5$=3,5-dichloro-4-pyridyl, and X=O) (423 mg, 1 mmol) was dissolved in methanol (4 ml), A 1N aqueous NaOH solution (2 ml) was added to the solution. The mixture was stirred for two hours at room temperature and the reaction mixture was poured into a 5% aqueous ammonium chloride solution. Precipitated crystals were collected by filtration, washed, and recrystallized from ethanol, to thereby obtain the title compound (240 mg, yield 59%), Melting point: 178–180° C. (decomposition)

$^1$-NMR(CDCl$_3$) δ: 1.40–2.00(8H, m), 3.77(3H, s), 4.58–4.80(1H, m), 6.78(1H, s), 7.50(1H, s), 7.94(1H, s), 8.56(2H, s).

Example 32

The procedure of Example 1 was repeated through use of 4-cyclopentyloxy-5-methoxy-2-pyridineacetonitrile (3a) and 3-nitrobenzaldehyde, to thereby obtain the compound shown below.

(Z) -2-(4-Cyclopentyloxy-5-methoxy-2-pyridyl)-3-(3-nitrophenyl)propenenitrile (formula (1), wherein $R^1$=cyclopentyl, $R^2$=CH$_3$, $R^3$=CN, $R^4$=H, $R^5$=3-nitrophenyl, and X=O), Melting point: 126–127° C.

$^1$-NMR(CDCl$_3$) δ: 1.50–2.20(8H, m), 3.98(3H, s), 4.82–5.10(1H, m), 7.28(1H, s), 7.67(1H, t, J=8.0 Hz), 8.16 (1H, s), 8.20–8.40(3H, m), 8.60–8.70(1H, m).

Example 33

The procedure of Example 1 was repeated through use of 4-cyclopentyloxy-5-methoxy-2-pyridineacetonitrile (3a) and 3-fluoro-4-pyridinecarbaldehyde (Preparation Example 12), to thereby obtain the compound shown below.

(Z)-2-(4-Cyclopentyloxy-5-methoxy-2-pyridyl)-3-(3-fluoro-4-pyridyl)propenenitrile (formula (1), wherein $R^1$=cyclopentyl, $R^2$=CH$_3$, $R^3$=CN, $R^4$=H, $R^5$=3-fluoro-4-pyridyl, and X=0), Melting point: 120–121° C.

$^1$-NMR(CDCl$_3$) δ: 1.60–2.15(8H, m), 3.98(3H, s), 4.92–4.97(1H, m), 7.28(1H, s), 8.10(1H, t, J=6.0 Hz), 8.18 (1H, s), 8.47(1H, s), 8.56(1H, d, J=5 Hz), 8.60(1H, d, J=2 Hz).

Example 34

The procedure of Example 1 was repeated through use of 4-(2-indanyloxy)-5-methoxy-2-pyridineacetonitrile (3h) and methyl 4-formyl-2-picolinate, to thereby obtain the compound shown below.

(Z)-2-[4-(2-Indanyloxy-5-methoxy-2-pyridyl]-3-(2-methoxycarbonyl-4-pyridyl)propenenitrile (formula (1), wherein $R^1$=2-indanyl, $R^2$=CH$_3$, $R^3$=CN, $R^4$=H, $R^5$=2-methoxycarbonyl-4-pyridyl, and X=O), Melting point: 177–179° C.

$^1$-NMR(CDCl$_3$) δ: 3.14–3.85(4H, m), 3.93(3H, s), 4.05 (3H, s), 5.29–5.36(1H, m), 7.24–7.37(5H, m), 8.01–8.09 (1H, m), 8.18(1H, s), 8.35(1H, s), 8.47(1H, s), 8.89(1H, d, J=5.0 Hz).

Example 35

The procedure of Example 1 was repeated through use of 4-(2-indanyloxy)-5-methoxy-2-pyridineacetonitrile (3h) and 4-pyridinecarbaldehyde, to thereby obtain the compound shown below.

(Z)-2-[4-(2-Indanyloxy)-5-methoxy-2-pyridyl]-3-(4-pyridyl)propenenitrile (formula (1), wherein $R^1$=2-indanyl, $R^2$=CH$_3$, $R^3$=CN, $R^4$=H, $R^5$=4-pyridyl, and X=O), Melting point: 205–206° C.

$^1$-NMR(CDCl$_3$) δ: 3.15–3.75(4H, m), 3.92(3H, s), 5.20–5.50(1H, m), 7.24(4H, s), 7.36(1H, s), 7.75(2H, d, J=7.0 Hz), 8.17(1H, s), 8.28(1H, s), 8.78(2H, d, J=7.0 Hz).

Example 36

The procedure of Example 1 was repeated through use of 4-(2-indanyloxy)-5-methoxy-2-pyridineacetonitrile (3h) and 4-pyridinecarbaldehyde N-oxide, to thereby obtain the compound shown below.

4-[(Z)-2-Cyano-2-(4-(2-indanyloxy)-5-methoxy-2-pyridyl)-1-ethenyl]pyridine N-oxide (formula (1), wherein $R^1$=2-indanyl, $R^2$=$CH_3$, $R^3$=CN, $R^4$=H, $R^5$=1-oxo-4-pyridyl, and X=O).

Melting point: 231–232° C.

$^1$H-NMR(CDCl$_3$) δ: 3.15–3.72(4H, m), 3.92(3H, s), 5.20–5.45(1H, m), 7.24(4H, s), 7.33(1H, s), 7.85(2H, d, J=7.0 Hz), 8.10–8.30(4H, m).

Example 37

The procedure of Example 1 was repeated through use of 4-(2-indanyloxy)-5-methoxy-2-pyridineacetonitrile (3h) and 3,5-dichloro-4-pyridinecarbaldehyde N-oxide (Preparation Example 13), to thereby obtain the compound shown below.

4-[(Z)-2-Cyano-2-(4-(2-indanyloxy)-5-methoxy-2-pyridyl)-1-ethenyl]-3,5-dichloropyridine N-oxide (formula (1), wherein $R^1$=2-indanyl, $R^2$=$CH_3$, $R^3$=CN, $R^4$=H, $R^5$=3,5-dichloro-1-oxo-4-pyridyl, and X=O).

Melting point: 229–230° C.

$^1$H-NMR(CDCl$_3$) δ: 3.10–3.72(4H, m), 3.93(3H, s), 5.20–5.43(1H m), 7.23(5H, s), 8.13(1H, s), 8.20(1H, s), 8.26(2H, s).

Example 38

Synthesis of (Z)-3-(3-carboxyphenyl)-2-(4-cyclopentyloxy-5-methoxy-2-pyridyl)propenenitrile (formula (1), wherein $R^1$=cyclopentyl, $R^2$=$CH_3$, $R^3$=CN, $R^4$=H, $R^5$=3-carboxyphenyl, and X=O):

4-Cyclopentyloxy-5-methoxy-2-pyridineacetonitrile (3a) (4.64 g, 20 mmol) and 3-formylbenzoic acid (3.00 g, 20 mmol) were dissolved in methanol (60 ml), While the solution was stirred at 5° C., 1 M aqueous $CH_3$ONa-$CH_3$OH solution (46 ml) was added dropwise. The reaction mixture was stirred for 30 minutes under the same conditions and was poured into a 5% aqueous ammonium chloride solution. Precipitated crystals were collected by filtration, washed, and recrystallized from ethanol, to thereby obtain the title compound (4.00 g, yield 55%), Melting point: 253–254° C.

$^1$-NMR(DMSO-d$_6$) δ: 1.50–2.20(8H, m), 3.90(3H, s), 4.98–5.20(1H, m), 7.49(1H, s), 7.67(1H, t, J=7.5 Hz), 8.00–8.30(2H, m), 8.25(1H, s), 8.35(1H, s), 8.56(1H, s).

Example 39

The procedure of Example 23 was repeated through use of 4-cyclopentyloxy-5-methoxy-2-pyridinecarbaldehyde and methyl 3-cyanomethylbenzoate, to thereby obtain the compound shown below.

(Z)-3-(4-Cyclopentyloxy-5-methoxy-2-pyridyl)-2-(3-methoxycarbonylphenyl)propenenitrile (formula (1), wherein $R^1$=cyclopentyl, $R^2$=$CH_3$, $R^3$=H, $R^4$=CN, $R^5$=3-methoxycarbonylphenyl, and X=O), Melting point: 116–117° C.

$^1$-NMR(CDCl$_3$) δ: 1.55–2.30(8H, m), 3.96(3H, s) 4.00 (3H, s), 4.80–5.10(H, m), 7.42–8.50(7H, m).

EXAMPLE 40

The procedure of Example 23 was repeated through use of 4-(2-indanyloxy)-5-methoxy-2-pyridinecarbaldehyde (Preparation Example 14) and methyl 3-cyanomethylbenzoate, to thereby obtain the compound shown below.

(Z)-3-[4-(2-Indanyloxy)-5-methoxy-2-pyridyl]-2-(3-methoxycarbonylphenyl) propenenitrile (formula (1), wherein $R^1$=2-indanyl, $R^2$=$CH_3$, $R^3$=H, $R^4$=CN, R,$^5$=3-methoxycarbonylphenyl, and X=O), Melting point: 183–184° C.

$^1$H-NMR(DMSO-d$_6$) δ: 3.10–3.70(4H, m), 3.94(3H, s), 3.96(3H, s), 5.20–5.40(1H, m), 7.23(4H, s), 7.40–8.40(7H, m)

Example 41

The procedure of Example 23 was repeated through use of 4-(2-indanyloxy)-5-methoxy-2-pyridinecarbaldehyde (Preparation Example 14) and 4-pyridineacetonitrile, to thereby obtain the compound shown below.

(Z)-3-[4-(2-Indanyloxy)-5-methoxy-2-pyridyl]-2-(4-pyridyl)propenenitrile (formula (1), wherein $R^1$=2-indanyl, $R^2$=$CH_3$, $R^3$=H, $R^4$=CN, $R^5$=4-pyridyl, and X=O), Melting point: 195–197° C.

$^1$-NMR(CDCl$_3$) δ: 3.10–3.75(4H, m), 3.96(3H, s), 5.20–5.45(1H, m), 7.23(4H, s), 7.62(2H, d, J=6.0 Hz), 7.82(1H, s), 7.87(1H, s), 8.29(1H, s), 8.73(2H, d, J=6.0 Hz).

EXAMPLE 42

The procedure of Example 28 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and methyl bromoacetate, to thereby obtain the compound shown below.

(Z)-3-(3,5-Dichloro-4-pyridyl)-2-(5-methoxy-4-methoxycarbonylmethyloxy-2-pyridyl)propenenitrile (formula (1), wherein $R^1$=$CH_2CO_2CH_3$, $R^2$=$CH_3$, $R^3$=CN, $R^4$=H, $R^5$=3,5-dichloro-4-pyridyl, and X=O).

Melting point: 131–132° C.

$^1$-NMR(CDCl$_3$) δ: 3.85(3H, s), 4.04(3H, s), 4.84(2H, s), 7.14(1H, s), 8.19(1H, s), 8.27(1H, s), 8.61(2H, s),

Example 43

The procedure of Example 28 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and 2-bromoethanol, to thereby obtain the compound shown below.

(Z)-3-(3,5-Dichloro-4-pyridyl)-2-[4-(2-hydroxyethyloxy)-5-methoxy-2-pyridyl)propenenitrile (formula (1), wherein $R^1$=$(CH_2)_2$OH, $R^2$=$CH_3$, $R^3$=CN, $R^4$=H, $R^5$=3,5-dichloro-4-pyridyl, and X=O), Melting point: 159–160° C.

$^1$H-NMR(CDCl$_3$) δ: 2.24(1H, t, J=6.0 Hz), 4.01(3H, s), 4.04–4.08(2H, m), 4.27(2H, t, J=4.0 Hz), 7.29(1H, s), 8.19 (1H, s), 8.24(1H, s), 8.61(2H, s),

Example 44

The procedure of Example 28 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and 4-bromobutanol, to thereby obtain the compound shown below.

(Z)-3-(3,5-Dichloro-4-pyridyl)-2-[4-(4-hydroxybutyloxy-5-methoxy-2-pyridyl)propenenitrile (formula (1), wherein $R^1$=$(CH_2)_4$OH, $R^2$=$CH_3$, $R^3$=CN, $R^4$=H, $R^5$=3,5-dichloro-4-pyridyl, and X=O).

Melting point: 120. 5–122° C.

¹H-NMR(CDCl₃) δ: 1.74–1.82(3H, m), 1.99–2.05(2H, m), 3.75(2H, m), 4.00(3H, s), 4.21(2H, t, J=6.0 Hz), 7.27 (1H, s), 8.19(1H, s), 8.21(1H, s), 8.61(2H, s),

Example 45

The procedure of Example 28 was repeated through use of (Z)-3-(3,5-dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) and 5-bromopentanol, to thereby obtain the compound shown below.

(Z)-3-(3,5-Dichloro-4-pyridyl)-2-[4-(5-hydroxypentyloxy)-5-methoxy-2-pyridyl)propenenitrile (formula (1), wherein $R^1$=(CH₂)₅OH, $R^2$=CH₃, $R^3$=CN, $R^4$=H, $R^5$=3,5-dichloro-4-pyridyl, and X=O), Melting point: 86–87° C.

¹H-NMR(CDCl₃) δ: 1.35(1H, m), 1.58–1.70(4H, m), 1.93–1.97(2H, m), 3.71(2H, m), 4.00(3H, s), 4.16(2H, t, J=6.0 Hz), 7.26(1H, s), 8.19(1H, s), 8.21(1H s), 8.61(2H, s).

Example 46

Synthesis of (Z)-3-(3,5-dichloro-4-pyridyl)-2-[5-methoxy-4-(3,4-methylenedioxyphenylmethyloxy)-2-pyridyl]propenenitrile (formula (1), wherein $R^1$=3,4-methylenedioxyphenylmethyl, $R^2$=CH₃, $R^3$=CN, $R^4$=H, $R^5$=3,5-dichloro-4-pyridyl, and X=O):

(Z)-3-(3,5-Dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) (0.97 g, 3.0 mmol), 3,4-methylenedioxyphenylmethanol (0.50 g, 3.3 mmol), and triphenylphosphine (1.18 g, 4.5 mmol) were dissolved in tetrahydrofuran (100 ml), While the solution was stirred at room temperature, diethyl azodicarboxylate (0.78 g, 4.5 mmol) was added dropwise. The reaction mixture was stirred for four hours at room temperature and then water was added thereto. The mixture was extracted with ethyl acetate. The organic layer was sequentially washed with water and saturated brine, dried, and then concentrated under reduced pressure. Crystals precipitated from the residue were recrystallized from an isopropyl ether-ethanol, to thereby obtain the title compound (1.01 g, yield 74%), Melting point: 182–183° C.

¹-NMR(CDCl₃) δ: 4.00(3H, s), 5.15(2H, s), 5.98(2H, s), 6.80–7.00(3H, m) 7.36(1H, s), 8.16(1H, s), 8.23(1H, s), 8.61(2H, s).

Example 47

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) and 4,5-dimethoxy-2-pyridinemethanol, to thereby obtain the compound shown below.

(Z)-3-(3,5-Dichloro-4-pyridyl)-2-[4-(4,5-dimethoxy-2-pyridylmethyloxy)-5-methoxy-2-pyridyl]propenenitrile (formula (1), wherein $R^1$=4,5-dimethoxy-2-pyridylmethyl, $R^2$=CH₃, $R^3$=CN, $R^4$=H, $R^5$=3,5-dichloro-4-pyridyl, and X=O).

Melting point: 146.5–147.5° C.

¹-NMR(CDCl₃) δ: 3.94(3H, s), 3.96(3H, s), 4.03(3H, s), 5.31(2H, s), 7.07(1H, s), 7.52(1H, s), 8.09(1H, s), 8.14(1H, s), 8.24(1H, s), 8.60(2H, s).

Example 48

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) and cyclopropanemethanol, to thereby obtain the compound shown below.

(Z)-2-(4-Cyclopropylmethyloxy-5-methoxy-2-pyridyl)-3-(3,5-dichloro-4-pyridyl)propenenitrile (formula (1), wherein $R^1$=cyclopropylmethyl, $R^2$=CH₃, $R^3$=CN, $R^4$=H, $R^5$=3,5-dichloro-4-pyridyl, and X=O), Melting point: 118–119° C.

¹-NMR(CDCl₃) δ: 0.44(2H, m), 0.72(2H, m), 1.36(1H, m), 3.99(2H, d, J=7.5 Hz), 4.02(3H, s), 7.23(1H, s), 8.19 (1H, s), 8.23(1H, s), 8.61(2H, s).

Example 49

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) and 2-pyridineethanol, to thereby obtain the compound shown below.

(Z)-3-(3,5-Dichloro-4-pyridyl)-2-[5-methoxy-4-(2-(2-pyridyl)ethyloxy)-2-pyridyl]propenenitrile (formula (1), wherein $R^1$=2-(2-pyridyl)ethyl, $R^2$=CH₃, $R^3$=CN, $R^4$=H, $R^5$=3,5-dichloro-4-pyridyl, and X=O), Melting point: 134–135° C.

¹-NMR(CDCl₃) δ: 3.38(2H, t, J=7.0 Hz), 3.96(3H, s), 4.58(2H, t, J=7.0 Hz), 7.00–7.30(2H, m), 7.32(1H, s), 7.65 (1H, m), 8.15(1H, s), 8.21(1H, s), 8.55(1H, m), 8.61(2H, s).

Example 50

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) and 4-methyl-5-thiazoleethanol, to thereby obtain the compound shown below.

(Z)-3-(3,5-Dichloro-4-pyridyl)-2-[5-methoxy-4-(2-(4-methyl-5-thiazolyl)ethyloxy)-2-pyridyl]propenenitrile (formula (1), wherein $R^1$=2-(4-methyl-5-thiazolyl)ethyl, $R^2$=CH₃, $R^3$=CN, $R^4$=H, $R^5$=3,5-dichloro-4-pyridyl, and X=O).

Melting point: 136–137° C.

¹H-NMR(CDCl₃) δ: 2.48(3H, s), 3.36(2H, t, J=7.0 Hz), 4.00(3H, s), 4.31(2H, t, J=7.0 Hz), 7.22(1H, s), 8.18(1H, s), 8.23(1H, s), 8.61(2H, s), 8.61(1H, s).

Example 51

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=CH₃, $R^3$=CN, $R^4$=H, $R^5$=3,5-dichloro-4-pyridyl, and X=O) and N-hydroxyethyl-2-pyridone (Preparation Example 15), to thereby obtain the compound shown below.

(Z)-3-(3,5-Dichloro-4-pyridyl)-2-[5-methoxy-4-(2-(2-pyridon-1-yl)ethyloxy)-2-pyridyl]propenenitrile (formula (1), wherein $R^1$=2-(2-pyridon-1-yl)ethyl, $R^2$=CH₃, $R^3$=CN, $R^4$=H, $R^5$=3,5-dichloro-4-pyridyl, and X=O).

Melting point: 142–143° C.

¹-NMR(CDCl₃) δ: 3.97(3H, s), 4.41(2H, t, J=5.0 Hz), 4.48(2H, t, J=5.0 Hz), 6.17–6.22(1H, m), 6.58(1H, d, J=10.0 Hz), 7.26(1H, s), 7.32–7.40(1H, m), 7.45(1H, dd, J=2.0, 7.0 Hz), 8.10(1H, s), 8.22(1H, s), 8.60(2H, s).

Example 52

The procedure of Example 46 was repeated through use of (Z)-3-(3,5-dichloro-4-pyridyl)-2-(4-hydroxy-5-methoxy-2- pyridyl)propenenitrile (formula (1), wherein $R^1$=H, $R^2$=$CH_3$, $R^3$=CN, $R^4$=H, $R^5$=3,5-dichloro-4-pyridyl, and X=O) and 3-pyridinepropanol, to thereby obtain the compound shown below.

(Z)-3-(3,5-Dichloro-4-pyridyl)-2-[5-methoxy-4-(3-(3-pyridyl)propyloxy)-2-pyridyl]propenenitrile (formula (1), wherein $R^1$=3-(3-pyridyl)propyl, $R^2$=$CH_3$, $R^3$=CN, $R^4$=H, $R^5$=3,5-dichloro-4-pyridyl, and X=O), Melting point: 91–93° C.

$^1$-NMR(DMSO-$d_6$) δ: 2.12(2H, m), 2.79(2H, t, J=6.5 Hz), 3.95(3H, s), 4.21(2H, t, J=6.5 Hz), 7.30(1H, m), 7.56(1H, s), 7.67(1H, m), 8.28(1H, s), 8.33(1H, s), 8.47(2H, s), 8.82(2H, s).

Example 53

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and 4-pyridinepropanol, to thereby obtain the compound shown below.

(Z)-3-(3,5-Dichloro-4-pyridyl)-2-[5-methoxy-4-(3-(4-pyridyl)propyloxy)-2-pyridyl]propenenitrile (formula (1), wherein $R^1$=3-(4-pyridyl)propyl, $R^2$=$CH_3$, $R^3$=CN, $R^4$=H, $R^5$=3,5-dichloro-4-pyridyl, and X=O).

Melting point: 124–125° C.

$^1$-NMR(CDCl$_3$) δ: 2.25(2H, m), 2.87(2H, m), 4.01(3H, s), 4.16(2H, t, J=6.0 Hz), 7.17(2H, d, J=6.0 Hz), 7.22(1H, s), 8.19(1H, s), 8.23(1H, s), 8.50(2H, d, J=6.0 Hz), 8.61(2H, s).

Example 54

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and N-hydroxyethylmorpholine, to thereby obtain the compound shown below.

(Z)-3-(3,5-Dichloro-4-pyridyl)-2-[5-methoxy-4-(2-(N-morpholino)ethyloxy)-2-pyridyl]propenenitrile (formula (1), wherein $R^1$=2-(N-morpholino)ethyl, $R^2$=$CH_3$, $R^3$=CN, $R^4$=H, $R^5$=3,5-dichloro-4-pyridyl, and X=O).

Melting point: 130–131° C.

$^1$-NMR(CDCl$_3$) δ: 2.50–2.70(4H, m), 2.89(2H, t, J=6.0 Hz), 3.60–3.82(4H, m), 4.00(3H, s), 4.28(2H, t, J=6.0 Hz), 7.29(1H, s), 8.19(1H, s), 8.22(1H, s), 8.61(2H, s).

Example 55

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and 1,3-bis(BOC-amino)-2-propanol, to thereby obtain the compound shown below.

(Z)-2-[4-(1,3-bis(BOC-amino)-2-propyloxy)-5-methoxy-2-pyridyl]-3-(3,5-dichloro-4-pyridyl)propenenitrile (formula (1), wherein $R^1$=1,3-bis(BOC-amino)-2-propyl, $R^2$=$CH_3$, $R^3$=CN, $R^4$=H, $R^5$=3,5-dichloro-4-pyridyl, and X=O), Melting point: 181–181.5° C.

$^1$-NMR(CDCl$_3$) δ: 1.43(18H, s), 3.23(2H, m), 3.66(2H, m), 3.99(3H, s), 4.54(1H, m), 5.21(2H, m), 7.93(1H, s), 8.16(1H, s), 8.25(1H, s), 8.60(2H, s).

Example 56

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and cis-1,3-cyclopentanediol monoTBS-ether, to thereby obtain the compound shown below.

(Z)-3-(3,5-Dichloro-4-pyridyl)-2-[5-methoxy-4-(cis-3-(TBS-oxy)cyclopentyloxy-2-pyridyl]propenenitrile (formula (1), wherein $R^1$=cis-3-(TBS-oxy)cyclopentyl, $R^2$=$CH_3$, $R^3$=CN, $R^4$=H, $R^5$=3,5-dichloro-4-pyridyl, and X=O), $^1$-NMR(CDCl$_3$) δ: 0.05(6H, s), 0.88(9H, s), 1.60–2.62(6H, m), 3.98(3H, s), 4.20–4.40(1H, m), 4.75–5.00(1H, m), 7.19(1H, s), 8.19(2H, s), 8.61(2H, s).

Example 57

The procedure of Example 46 was repeated through use of (Z)-3-(3,5-dichloro-4-pyridyl)-2-(4-hydroxy-5-methoxy-2-pyridyl)propenenitrile (formula (1), wherein $R^1$=H, $R^2$=$CH_3$, $R^3$=CN, $R^4$=H, $R^5$=3,5-dichloro-4-pyridyl, and X=O) and trans-1,3-cyclopentanediol monoTBS-ether, to thereby obtain the compound shown below.

(Z)-3-(3,5-Dichloro-4-pyridyl)-2-[5-methoxy-4-(trans-3-(TBS-oxy)cyclopentyloxy-2-pyridyl]propenenitrile (formula (1), wherein $R^1$=trans-3-(TBS-oxy)cyclopentyl, $R^2$=$CH_3$, $R^3$=CN, $R^4$=H, $R^5$=3,5-dichloro-4-pyridyl, and X=O).

$^1$H-NMR(CDCl$_3$) δ: 0.06(6H, s), 0.89(9H, s), 1.50–2.50(6H, m), 3.98(3H, s), 4.30–4.60(1H, m), 4.95–5.22(1H, m), 7.23(1H, s), 8.17(1H, s), 8.20(1H, s), 8.61(2H, s).

Example 58

Synthesis of (Z)-2-(3-carboxyphenyl)-3-[4-(2-indanyloxy)-5-methoxy-2-pyridyl]propenenitrile (formula (1), wherein $R^1$=2-indanyl, $R^2$=$CH_3$, $R^3$=H, $R^4$=CN, $R^5$=3-carboxyphenyl, and X=O):

In 4 ml of dioxane, was dissolved (Z)-3-[4-(2-indanyloxy)-5-methoxy-2-pyridyl]-2-(3-methoxycarbonylphenyl)propenenitrile (formula (1), wherein $R^1$=2-indanyl, $R^2$=$CH_3$, $R^3$=H, $R^4$=CN, $R^5$=3-methoxycarbonylphenyl, and X=O) (426 mg, 1 mmol), To the solution was added 1N aqueous NaOH solution (1.2 ml), The mixture was stirred for 0.5 hours at room temperature. The reaction mixture was poured into 5% aqueous ammonium chloirde solution. Precipitated crystals were collected by filtration, washed with water, and recrystallized from ethanol, to thereby obtain the title compound (353 mg, yield 86%), Melting point: 281.5–282.5° C.

$^1$-NMR(DMSO-$d_6$) δ: 2.90–3.65(4H, m), 3.89(3H, s), 5.20–5.42(1H, m), 7.05–7.40(4H, m), 7.50–7.75(2H, m), 7.90–8.10(3H, m), 8.37(2H, s).

Example 59

The procedure of Example 58 was repeated through use of (Z)-2-[4-(2-indanyloxy)-5-methoxy-2-pyridyl]-3-(2-methoxycarbonyl-4-pyridyl)propenenitrile (formula (1), wherein $R^1$=2-indanyl, $R^2$=$CH_3$, $R^3$=CN, $R^4$=H, $R^5$=2-methoxycarbonyl-4-pyridyl, and X=O), to thereby obtain the compound shown below.

(Z)-3-(2-Carboxy-4-pyridyl)-2-[4-(2-indanyloxy)-5-methoxy-2-pyridyl]propenenitrile (formula (1), wherein $R^1$=2-indanyl, $R^2$=$CH_3$, $R^3$=CN, $R^4$=H, $R^5$=2-carboxy-4-pyridyl, and X=O), Melting point: 224–225° C.

$^1$-NMR(DMSO-$d_6$) δ: 3.08–3.56(4H, m), 3.85(3H, s), 5.50(1H, br), 7.18–7.30(4H, m), 7.66(1H, s), 8.09–8.10(1H, m), 8.29(1H, s), 8.39(1H, s), 8.53(1H, s), 8.89(1H, d, J=5.3 Hz).

Example 60

The procedure of Example 58 was repeated through use of (Z)-3-(4-cyclopentyloxy-5-methoxy-2-pyridyl)-2-(3-methoxycarbonylphenyl)propenenitrile (formula (1), wherein $R^1$=cyclopentyl, $R^2$=$CH_3$, $R^3$=H, $R^4$=CN, $R^5$=3-methoxycarbonylphenyl, and X=O), to thereby obtain the compound shown below.

(Z)-2-(3-Carboxyphenyl)-3-(4-cyclopentyloxy-5-methoxy-2-pyridyl)propenenitrile (formula (1), wherein $R^1$=cyclopentyl, $R^2$=$CH_3$, $R^3$=H, $R^4$=CN, $R^5$=3-carboxyphenyl, and X=O).

Melting point: 264–266° C.

$^1$-NMR(DMSO-$d_6$) δ: 1.58–1.82(6H, m), 1.97–2.10(2H, m), 3.94(3H, s), 4.88–4.94(1H, m), 7.54(1H, s), 7.63(1H, t, J=8.0 Hz), 7.96–8.03(3H, m), 8.33(1H, s), 8.35(1H, s).

Example 61

Synthesis of (Z)-2-[4-(1,3-diamino-2-propyloxy)-5-methoxy-2-pyridyl]-3-(3,5-dichloro-4-pyridyl)propenenitrile trihydrochloride (formula (1), wherein $R^1$=1,3-diamino-2-propyl, $R^2$=$CH_3$, $R^3$=CN, $R^4$=H, $R^5$=3,5-dichloro-4-pyridyl, and X=O):

In 4 ml of ether, was dissolved (Z)-2-[4-(1,3-bis(BOC-amino)-2-propyloxy)-5-methoxy-2-pyridyl]-3-(3,5-dichloro-4-pyridyl)propenenitrile (formula (1), wherein $R^1$=1,3-bis(BOC-amino)-2-propyl, $R^2$=$CH_3$, $R^3$=CN, $R^4$=H, $R^5$=3,5-dichloro-4-pyridyl, and X=O) (594 mg, 1 mmol). To the solution was added 4N HCl-dioxane solution (2 ml), The mixture was stirred for three hours at room temperature. Precipitated crystals were collected by filtration, washed with ether, and recrystallized from ethanol, to thereby obtain the title compound (450 mg, yield 89%), Melting point: 174–177° C.

$^1$-NMR(DMSO-$d_6$) δ: 3.23(2H, m), 3.40(2H, m), 3.97 (3H, s), 5.32(1H, m), 8.22(1H, s), 8.41(1H, s), 8.72(1H, s), 8.83(2H, s).

Example 62

Synthesis of (Z)-3-(3,5-dichloro-4-pyridyl)-2-[4-(cis-(3-hydroxy)cyclopentyloxy)-5-methoxy-2-pyridyl]propenenitrile (formula (1), wherein $R^1$=cis-(3-hydroxy) cyclopentyl, $R^2$=$CH_3$, $R^3$=CN, $R^4$=H, $R^5$=3,5-dichloro-4-pyridyl, and X=O):

In 2 ml of THF, was dissolved (Z)-3-(3,5-dichloro-4-pyridyl)-2-[5-methoxy-4-(cis-3-(TBS-oxy)cyclopentyloxy)-2-pyridyl]propenenitrile (formula (1), wherein $R^1$=cis-3-(TBS-oxy)cyclopentyl, $R^2$=$CH_3$, $R^3$=CN, $R^4$=H, $R^5$=3,5-dichloro-4-pyridyl, and X=O) (520 mg, 1 mmol). To the solution was added 1M tetrabutylammnoium fluoride-THF solution (2.2 ml), and the mixture was stirred for five hours at room temperature. The reaction mixture was evaporated to dryness and then water was added to the residue. The mixture was extracted with ethyl acetate. The organic layer was washed with saturated brine, dried, and then concentrated under reduced pressure. The residue was purified by silica gel column chromatography and recrystallized from a benzene-hexane, to thereby obtain the title compound (240 mg, yield 59%), Melting point: 134–135° C.

$^1$-NMR(CDCl$_3$) δ: 1.90–2.24(6H, m), 2.39(1H, d, J=8.0 Hz), 3.98(3H, s), 4.38–4.50(1H, m), 5.04–5.08(1H, m), 7.26(1H, s), 8.20(1H, s), 8.22(1H, s), 8.61(2H, s).

Example 63

The procedure of Example 62 was repeated through use of (Z)-3-(3,5-dichloro-4-pyridyl)-2-[5-methoxy-4-(trans-3-(TBS-oxy)cyclopentyloxy)-2-pyridyl]propenenitrile (formula (1), wherein $R^1$=trans-3-(TBS-oxy)cyclopentyl, $R^2$=$CH_3$, $R^3$=CN, $R^4$=H, $R^5$=3,5-dichloro-4-pyridyl, and X=O), to thereby obtain the compound shown below.

(Z)-3-(3,5-Dichloro-4-pyridyl)-2-[4-(trans-(3-hydroxy) cyclopentyloxy)-5-methoxy-2-pyridyl]propenenitrile (formula (1), wherein $R^1$=trans-(3-hydroxy)cyclopentyl, $R^2$=$CH_3$, $R^3$=CN, $R^4$=H, $R^5$=3,5-dichloro-4-pyridyl, and X=O), Melting point: 136–137° C.

$^1$-NMR(CDCl$_3$) δ: 1.58(1H, br), 1.70–1.80(1H, m), 1.90–2.00(1H, m), 2.07–2.28(3H, m), 2.35–2.46(1H, m), 3.98(3H, s), 4.58–4.62(1H, m), 5.04–5.07(1H, m), 7.24(1H, s), 8.17(1H, s), 8.20(1H, s), 8.61(2H, s).

Example 64

The procedure of Example 1 was repeated through use of 5-cyclopentyloxy-6-methoxy-3-pyridineacetonitrile (Preparation Example 16) and 3,5-dichloro-4-pyridinecarbaldehyde (Preparation Example 7), to thereby obtain the compound shown below.

(Z)-2-(5-Cyclopentyloxy-6-methoxy-3-pyridyl)-3-(3,5-dichloro-4-pyridyl)propenenitrile.

Melting point: 143–144° C.

$^1$-NMR(CDCl$_3$) δ: 1.60–2.05(8H, m), 4.05(3H, s), 4.86 (1H, m), 7.25(1H, d, J=2.0 Hz) 7.27(1H, s), 8.11(1H, d, J=2.0 Hz), 8.62(2H, s).

Example 65

The procedure of Example 1 was repeated through use of 6-cyclopentyloxy-5-methoxy-2-pyridineacetonitrile (Preparation Example 17) and 3,5-dichloro-4-pyridinecarbaldehyde (Preparation Example 7), to thereby obtain the compound shown below.

(Z)-2-(6-Cyclopentyloxy-5-methoxy-2-pyridyl)-3-(3,5-dichloro-4-pyridyl)propenenitrile.

Melting point: 137–138° C.

$^1$-NMR(CDCl$_3$) δ: 1.61–2.12(8H, m), 3.91(3H, s), 5.50 (1H, m), 7.06(1H, d, J=8.0 Hz), 7.31(1H, d, J=8.0 Hz), 8.07(1H, s), 8.60(2H, s).

Example 66

The procedure of Example 1 was repeated through use of 5-methoxy-4-[2-(4-methyl-5-thiazolyl)ethyloxy]-2-pyridineacetonitrile (Preparation Example 18) and methyl 4-formyl-2-picolinate, to thereby obtain the compound shown below.

(Z)-2-[5-methoxy-4-(2-(4-methyl-5-thiazolyl)ethyloxy)-2-pyridyl]-3-(2-methoxycarbonyl-4-pyridyl)propenenitrile (formula (1), wherein $R^1$=2-(4-methyl-5-thiazolyl)ethyl, $R^2$=$CH_3$, $R^3$=CN, $R^4$=H, $R^5$=2-methoxycarbonyl-4-pyridyl, and X=O).

Melting point: 161–162° C.

$^1$-NMR(CDCl$_3$) δ: 2.49(3H, s), 3.37(2H, t, J=6.5 Hz), 4.01(3H, s), 4.05(3H, s), 4.32(2H, t, J=6.5 Hz), 7.25(1H, s), 8.04(1H, dd, J=1.0, 5.5 Hz), 8.20(1H, s), 8.34(1H, s), 8.47(1H, d, J=1.0 Hz), 8.63(1H, s), 8.89(1H, d, J=5.5 Hz).

Similarly, the following compounds can also be prepared.

(Z)-2-(6-Cyclopentyloxy-5-methoxy-2-pyridyl)-3-(2,6-dichlorophenyl)propenenitrile (Z)-2-(6-Cyclopentyloxy-5-methoxy-2-pyridyl)-3-(3-pyridyl)propenenitrile
(Z)-2-(6-Cyclopentyloxy-5-methoxy-2-pyridyl)-3-(4-pyridyl)propenenitrile
(Z)-3-(3,5-Dichloro-4-pyridyl)-2-(5-methoxy-6-phenethyloxy-2-pyridyl)propenenitrile
(Z)-3-(3,5-Dichloro-4-pyridyl)-2-(5-methoxy-6-(3-phenylpropyloxy)-2-pyridyl)propenenitrile
(Z)-2-(6-Butyloxy-5-methoxy-2-pyridyl)-3-(3,5-dichloro-4-pyridyl)propenenitrile
(Z)-3-(3,5-Dichloro-4-pyridyl)-2-[6-(1-ethylpropyloxy)-5-methoxy-2-pyridyl]propenenitrile
(Z)-3-(3,5-Dichloro-4-pyridyl)-2-[6-(2-indanyloxy)-5-methoxy-2-pyridyl]propenenitrile
(Z)-3-(3,5-Dichloro-4-pyridyl)-2-[5-methoxy-6-(tetrahydro-3-furanyloxy)-2-pyridyl]propenenitrile
(Z)-3-(3,5-Dichloro-4-pyridyl)-2-[5-methoxy-6-(exo-2-norbornyloxy)-2-pyridyl]propenenitrile
(Z)-3-(3,5-Dichloro-4-pyridyl)-2-(5-methoxy-6-methoxymethyloxy-2-pyridyl)propenenitrile
(Z)-3-(3,5-Dichloro-4-pyridyl)-2-(6-hydroxy-5-methoxypyridyl)propenenitrile
(Z)-3-(3,5-Dichloro-4-pyridyl)-2-[6-(3-hydroxypropyloxy)-5-methoxy-2-pyridyl]propenenitrile
(Z)-3-(6-Cyclopentyloxy-5-methoxy-2-pyridyl)-2-(3,5-dichloro-4-pyridyl)propenenitrile
(Z)-2-(6-Cyclopentyloxy-5-methoxy-2-pyridyl)-3-(3-fluoro-4-pyridyl)propenenitrile
(Z)-2-[6-(2-Indanyloxy)-5-methoxy-2-pyridyl]-3-(2-methoxycarbonyl-4-pyridyl)propenenitrile
(Z)-2-[6-(2-Indanyloxy)-5-methoxy-2-pyridyl]-3-(4-pyridyl)propenenitrile
4-[(Z)-2-Cyano-2-(6-(2-indanyloxy)-5-methoxy-2-pyridyl)-1-ethenyl]pyridine N-oxide
4-[(Z)-2-Cyano-2-(6-(2-indanyloxy)-5-methoxy-2-pyridyl)-1-ethenyl]-3,5-dichloropyridine N-oxide
(Z)-3-(3-Carboxyphenyl)-2-(6-cyclopentyloxy-5-methoxy-2-pyridyl)propenenitrile
(Z)-3-(6-Cyclopentyloxy-5-methoxy-2-pyridyl)-2-(3-methoxycarbonylphenyl)propenenitrile
(Z)-3-[6-(2-Indanyloxy)-5-methoxy-2-pyridyl]-2-(3-methoxycarbonylphenyl)propenenitrile
(Z)-3-[6-(2-Indanyloxy)-5-methoxy-2-pyridyl]-2-(4-pyridyl)propenenitrile
(Z)-3-(3,5-Dichloro-4-pyridyl)-2-[6-(2-hydroxyethyloxy)-5-methoxy-2-pyridyl]propenenitrile
(Z)-3-(3,5-Dichloro-4-pyridyl)-2-[6-(4-hydroxybutyloxy)-5-methoxy-2-pyridyl]propenenitrile
(Z)-3-(3,5-Dichloro-4-pyridyl)-2-[6-(5-hydroxypentyloxy)-5-methoxy-2-pyridyl]propenenitrile
(Z)-2-(6-Cyclopropylmethyloxy-5-methoxy-2-pyridyl)-3-(3,5-dichloro-4-pyridyl)propenenitrile
(Z)-3-(3,5-Dichloro-4-pyridyl)-2-[5-methoxy-6-(2-(2-pyridyl)ethyloxy)-2-pyridyl]propenenitrile
(Z)-3-(3,5-Dichloro-4-pyridyl)-2-[5-methoxy-6-(2-(4-methyl-5-thiazolyl)ethyloxy)-2-pyridyl]propenenitrile
(Z)-3-(3,5-Dichloro-4-pyridyl)-2-[5-methoxy-6-(2-(2-pyridone-1-yl)ethyloxy)-2-pyridyl]propenenitrile
(Z)-3-(3,5-Dichloro-4-pyridyl)-2-[5-methoxy-6-(3-(3-pyridyl)propyloxy)-2-pyridyl]propenenitrile
(Z)-3-(3,5-Dichloro-4-pyridyl)-2-[5-methoxy-6-(3-(4-pyridyl)propyloxy)-2-pyridyl]propenenitrile
(Z)-3-(3,5-Dichloro-4-pyridyl)-2-[5-methoxy-6-(2-(N-morholino)ethyloxy)-2-pyridyl]propenenitrile
(Z)-2-(3-Carboxyphenyl)-3-[6-(2-indanyloxy)-5-methoxy-2-pyridyl]propenenitrile
(Z)-3-(2-Carboxy-4-pyridyl)-2-[6-(2-indanyloxy)-5-methoxy-2-pyridyl]propenenitrile (Z)-2-(3-Carboxyphenyl)-3-(6-cyclopentyloxy-5-methoxy-2-pyridyl)propenenitrile
(Z)-2-[5-Methoxy-6-(2-(4-methyl-5-thiazolyl)ethyloxy)-2-pyridyl]-3-(2-methoxycarbonyl-4-pyridyl)propenenitrile
(Z)-3-(3,5-Dichloro-4-pyridyl)-2-[5-methoxy-6-(cis-3-(TBS-oxy)cyclopentyloxy)-2-pyridyl]propenenitrile
(Z) -3-(3,5-Dichloro-4-pyridyl) -2-[5-methoxy-6-(trans-3-(TBS-oxy)cyclopentyloxy)-2-pyridyl]propenenitrile
(Z)-3-(3,5-Dichloro-4-pyridyl)-2-[6-(cis-(3-hydroxy)cyclopentyloxy)-5-methoxy-2-pyridyl]propenenitrile
(Z)-3-(3,5-Dichloro-4-pyridyl)-2-[6-(trans-(3-hydroxy)cyclopentyloxy)-5-methoxy-2-pyridyl]propenenitrile
(Z)-2-(5-Cyclopentyloxy-6-methoxy-3-pyridyl)-3-(2,6-dichlorophenyl)propenenitrile
(Z)-2-(5-Cyclopentyloxy-6-methoxy-3-pyridyl)-3-(3-pyridyl)propenenitrile
(Z)-2-(5-Cyclopentyloxy-6-methoxy-3-pyridyl)-3-(4-pyridyl)propenenitrile
(Z)-3-(3,5-Dichloro-4-pyridyl)-2-(6-methoxy-5-phenethyloxy-3-pyridyl)propenenitrile
(Z)-3-(3,5-Dichloro-4-pyridyl)-2-[6-methoxy-5-(3-phenylpropyloxy)-3-pyridyl]propenenitrile
(Z)-2-(5-Butyloxy-6-methoxy-3-pyridyl)-3-(3,5-dichloro-4-pyridyl)propenenitrile
(Z)-3-(3,5-Dichloro-4-pyridyl)-2-[5-(1-ethylpropyloxy)-6-methoxy-3-pyridyl]propenenitrile
(Z)-3-(3,5-Dichloro-4-pyridyl)-2-[5-(2-indanyloxy)-6-methoxy-3-pyridyl]propenenitrile
(Z)-3-(3,5-Dichloro-4-pyridyl)-2-[6-methoxy-5-(tetrahydro-3-furanyloxy)-3-pyridyl]propenenitrile
(Z)-3-(3,5-Dichloro-4-pyridyl)-2-[6-methoxy-5-(exo-2-norbornyloxy)-3-pyridyl]propenenitrile
(Z)-3-(3,5-Dichloro-4-pyridyl)-2-(6-methoxy-5-methoxymethyloxy-3-pyridyl)propenenitrile
(Z)-3-(3,5-Dichloro-4-pyridyl)-2-(5-hydroxy-6-methoxy-3-pyridyl)propenenitrile
(Z)-3-(3,5-Dichloro-4-pyridyl)-2-[5-(3-hydroxypropyloxy)-6-methoxy-3-pyridyl]propenenitrile
(Z)-3-(5-Cyclopentyloxy-6-methoxy-3-pyridyl)-2-(3,5-dichloro-4-pyridyl)propenenitrile
(Z)-2-(5-Cyclopentyloxy-6-methoxy-3-pyridyl)-3-(3-fluoro-4-pyridyl)propenenitrile
(Z)-2-[5-(2-Indanyloxy)-6-methoxy-3-pyridyl]-3-(2-methoxycarbonyl-4-pyridyl)propenenitrile
(Z)-2-[5-(2-Indanyloxy)-6-methoxy-3-pyridyl]-3-(4-pyridyl)propenenitrile
4-[(Z)-2-Cyano-2-(5-(2-indanyloxy)-6-methoxy-3-pyridyl)-1-ethenyl]pyridine N-oxide
4-[(Z)-2-Cyano-2-(5-(2-indanyloxy)-6-methoxy-3-pyridyl)-1-ethenyl]-3,5-dichloropyridine N-oxide
(Z)-3-(3-Carboxyphenyl)-2-[5-cyclopentyloxy-6-methoxy-3-pyridyl]propenenitrile
(Z)-3-(5-Cyclopentyloxy-6-methoxy-3-pyridyl)-2-(3-methoxycarbonylphenyl)propenenitrile
(Z)-3-[5-(2-Indanyloxy)-6-methoxy-3-pyridyl]-2-(3-methoxycarbonylphenyl)propenenitrile
(Z)-3-[5-(2-Indanyloxy)-6-methoxy-3-pyridyl]-2-(4-pyridyl)propenenitrile
(Z)-3-(3,5-Dichloro-4-pyridyl)-2-[5-(2-hydroxyethyloxy)-6-methoxy-3-pyridyl]propenenitrile
(Z)-3-(3,5-Dichloro-4-pyridyl)-2-[5-(4-hydroxybutyloxy)-6-methoxy-3-pyridyl]propenenitrile
(Z)-3-(3,5-Dichloro-4-pyridyl)-2-[5-(5-hydroxypentyloxy)-6-methoxy-3-pyridyl]propenenitrile
(Z)-2-(5-Cyclopropylmethyloxy-6-methoxy-3-pyridyl)-3-(3,5-dichloro-4-pyridyl)propenenitrile
(Z)-3-(3,5-Dichloro-4-pyridyl)-2-[6-methoxy-5-(2-(2-pyridyl)ethyloxy)-3-pyridyl]propenenitrile (Z)-3-(3,5-Dichloro-4-pyridyl)-2-[6-methoxy-5-(2-(4-methyl-5-thiazolyl)ethyloxy)-3-pyridyl]propenenitrile
(Z)-3-(3,5-Dichloro-4-pyridyl)-2-[6-methoxy-5-(2-(2-pyridone-1-yl)ethyloxy)-3-pyridyl]propenenitrile
(Z)-3-(3,5-Dichloro-4-pyridyl)-2-[6-methoxy-5-(3-(3-pyridyl)propyloxy)-3-pyridyl]propenenitrile
(Z)-3-(3,5-Dichloro-4-pyridyl)-2-[6-methoxy-5-(3-(4-pyridyl)propyloxy)-3-pyridyl]propenenitrile
(Z)-3-(3,5-Dichloro-4-pyridyl)-2-[6-methoxy-5-(2-(N-morpholino)ethyloxy)-3-pyridyl]propenenitrile
(Z)-2-(3-Carboxyphenyl)-3-[5-(2-indanyloxy)-6-methoxy-3-pyridyl]propenenitrile
(Z)-3-(2-Carboxy-4-pyridyl)-2-[5-(2-indanyloxy)-6-methoxy-3-pyridyl]propenenitrile
(Z)-2-(3-Carboxyphenyl)-3-(5-cyclopentyloxy-6-methoxy-3-pyridyl)propenenitrile
(Z)-2-[6-Methoxy-5-(2-(4-methyl-5-thiazolyl)ethyloxy)-3-pyridyl]-3-(2-methoxycarbonyl-4-pyridyl)propenenitrile
(Z)-3-(3,5-Dichloro-4-pyridyl)-2-[6-methoxy-5-(cis-3-(TBS-oxy)cyclopentyloxy)-3-pyridyl]propenenitrile
(Z)-3-(3,5-Dichloro-4-pyridyl)-2-[6-methoxy-5-(trans-3-(TBS-oxy)cyclopentyloxy)-3-pyridyl]propenenitrile
(Z)-3-(35-Dichloro-4-pyridyl)-2-[5-(cis-(3-hydroxy)cyclopentyloxy)-6-methoxy-3-pyridyl]propenenitrile
(Z)-3-(3,5-Dichloro-4-pyridyl)-2-[5-(trans-(3-hydroxy)cyclopentyloxy) -6-methoxy-3-pyridyl]propenenitrile Test Example 1

PDE Inhibitory Activity Test

A variety of PDE isozymes shown below were isolated from human tissue and purified in accordance with the method described in literature.

PDE III Human platelet

H. Hidaka, et al., *Bioph. Bioch. Acta,* (1976), 429, p485
P. Grant, et al., *Biochemistry,* (1984), 23, p1801
PDE IV Human histocytic lymphoma (U-937)
T. Torphy, et al., *J. Pharm. Exp. Ther.,* (1992), 263, p1195
M. DiSanto, et al., *BBRC,* (1993), 197, p1126
PDE V Human platelet
H. Hidaka, et al., *Bioph. Bioch. Acta,* (1976), 429, p485
P. Grant, et al., *Biochemistry,* (1984), 23, p1801
C. D. Nicholson, et al., *Trends Pharmacol. Sci.,* (1991), 12, p19.

The PDE activity was determined through use of a modified two-step assay method described by Hidaka et al. (*Bioph. Bioch. Acta.,* (1976), 429, p485), Briefly, [$^3$H]cAMP and [$^3$H]cGMP are hydrolyzed by their respective PDE isozymes to form [$^3$H]5'-AMP and [$^3$H]5'-GMP, respectively. Subsequently, [$^3$H]5$^1$-AMP and [$^3$H]5$^1$-GMP are transformed into [$^3$H]adenosine and [$^3$H] guanosine, respectively, due to the action of nucleotidases. Unreacted [$^3$H]cAMP and [$^3$H]cGMP are removed, causing them to bond to ion exchange resin, and the quantity of eluted [$^3$H]adenosine or [$^3$H]guanosine was counted in a liquid scintillation counter.

The diluted enzyme solution contains 50 mM Tris-HCl (pH 8.0), 5 mM $MgCl_2$, and 50 μg of bovine serum albumin, wherein the concentrations represent final concentrations. The substrate concentration is 1 μM. The concentration of each test compound varies between 0.1 nM and 100 μM. Each test sample is incubated for 20 minutes at 30° C., and the PDE reaction is terminated by boiling for 2 minutes. The nucleotidase reaction was induced by adding snake venom nucleotidase to the above-described reaction mixture and incubating the resultant mixture for 20 minutes at 30° C.

The $IC_{50}$ values of the test compounds were obtained from concentration-reaction curves within the concentration range of 0.1 nM to 100 μM.

TABLE 1

| | PDE inhibitory Activity | | |
|---|---|---|---|
| Compound | PDE III $IC_{50}$ (μM) | PDE IV $IC_{50}$ (μM) | PDE V $IC_{50}$ (μM) |
| Example 1 | 10 | 0.0026 | >100 |
| Example 14 | >100 | 0.0059 | 5.6 |
| Example 15 | 91 | 0.0048 | 56 |
| Example 16 | 15 | 0.015 | 31 |
| Example 17 | >100 | 0.036 | >100 |
| Example 18 | 18 | 0.036 | 12 |
| Example 19 | >100 | 0.00065 | >100 |
| Example 20 | 56 | 0.011 | >100 |
| Rolipram | >100 | 5.0 | >100 |

Test Example 2

TNF-α Production Inhibition Test

Human promonocytic leukemia cells (U 937 cells, 1×10$^5$ cells/400 μl) were inoculated on a 24-well culture plate. By use of an RPMI 1640 culture liquid (supplemented with 10% FCS) containing 50 nM PMA, the cells were incubated for 72 hours, to thereby induce differentiation into monocyte/macrophage (see Sarkiz Daniel-Issakani, Allem M. Spiegel and Berta Strulovici (1989), *J. Biol. Chem.* 264, p20240–20247). Subsequently, the culture supernatant was discarded, and an RPMI 1640 culture liquid (supplemented with 10% FCS) containing 10 ng/ml of LPS (lipopolysaccharide; *E. coli,* 0111:B4) was added. Each compound was added one hour before the LPS treatment, so as to achieve concentrations of 100 μM, 10 μM, 1 μM, and 0.1 μM. Six hours after addition of LPS, the quantity of produced TNF-α in the supernatant was measured by use of a human TNF-α ELISA kit (Amersham, code RPN 2758), For respective doses of each compound, % control was calculated, wherein the quantity of TNF-α produced when LPS treatment was performed and the compound was not added was considered 100%. Further, based on primary regression curves, there were calculated $IC_{50}$ values in terms of TNF-α production inhibitory activity for respective compounds.

TABLE 2

| TNF-α Production Inhibition | |
|---|---|
| Compound | $IC_{50}$ (μM) |
| Example 1 | 10.2 |
| Example 4 | 7.6 |
| Example 10 | 10 |
| Example 11 | 5.5 |
| Example 16 | 13.1 |
| Example 19 | 2.9 |
| Example 20 | 7.1 |
| Example 21 | 13.3 |
| Rolipram | 100 |

Preparation Example 1

Tablet

| | |
|---|---|
| Compound of Example 1 | 50 mg |
| Crystalline cellulose | 50 mg |
| Lactose | 50 mg |
| Hydroxypropylcellulose | 18 mg |
| Magnesium stearate | 2 mg |
| Total | 170 mg |

Tablets each having the above composition were prepared through a customary method. If necessary, these tablets may be processed into sugar-coated tablets or film-coated tablets.

Preparation Example 2

Capsule

| | |
|---|---|
| Compound of Example 1 | 50 mg |
| Light silicic acid anhydride | 25 mg |
| Lactose | 100 mg |
| Starch | 50 mg |
| Talc | 25 mg |
| Total | 250 mg |

The above ingredients were filled in a No. 1 capsule, to thereby prepare capsule preparations.

Preparation Example 3

Granules

| | |
|---|---|
| Compound of Example 1 | 50 mg |
| Lactose | 600 mg |
| Cornstarch | 200 mg |
| Carboxymethylcellulose-Na | 20 mg |
| Hydroxypropylcellulose | 130 mg |
| Total | 1000 mg |

Granules of the above composition were prepared using a customary method.

Preparation Example 4

Powder

| | |
|---|---|
| Compound of Example 1 | 50 mg |
| Light silicic acid anhydride | 20 mg |
| Precipitated calcium carbonate | 10 mg |
| Lactose | 250 mg |
| Starch | 70 mg |
| Total | 400 mg |

A powder product having the above composition was prepared using a customary method.

Preparation Example 5

Injection

| | |
|---|---|
| Compound of Example 19 | 5 mg |
| Hydrogenated castor oil | 85 mg |
| Propylene glycol | 60 mg |
| Glucose | 50 mg |
| Distilled water for injection | Suitable amount |
| Total | 1 ml in total |

An injection having the above composition was prepared through a customary method.

Preparation Example 6

Intravenous Drip Infusion

| | |
|---|---|
| Compound of Example 19 | 50 mg |
| Glucose | 5 g |
| $Na_2HPO_4$ anhydrate | 10 mg |
| Citric acid | 14.5 mg |
| Distilled water for injection | Suitable amount |
| Total | 100 ml in total |

An intravenous drip infusion was prepared through a customary method.

INDUSTRIAL APPLICABILITY

The 2-substituted vinylpyridiene derivative of the present invention is endowed with strong and selective PDE IV inhibitory activity, and strong TNF-α production inhibitory activity. Thus, drugs designed on the basis of the selective PDE IV inhibitory activity are useful for the prevention and treatment of various diseases, including immediate or delayed asthma; allergies such as airway-hypersensitive allergy and other allergies stemming from the inhibition of activation of inflammatory blood cells such as eosinocytes; autoimmune diseases such as atopy and rheumatism; depression associated with disturbed metabolism of the cerebrum; cerebral infarction; senile dementia; and memory disorders associated with Parkinson's disease. Also, drugs designed on the basis of the TNF-α production inhibitory activity are useful for the prevention and treatment of various diseases, including rheumatism, osteoporosis, type I and type II diabetes, cancers, infections with HIV, AIDS, and shock caused by intracellular toxins. Moreover, since the compounds of the present invention have both selective PDE IV inhibitory action and TNF-α production inhibitory action, they are useful for the prevention and treatment of a wide variety of inflammatory diseases and autoimmune diseases.

We claim:

1. A substituted vinylpyridine compound represented by the following formula (1):

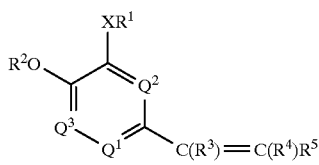
(1)

wherein $R^1$ represents a hydrogen atom, an alkyl group, an alkenyl group, a hydroxyalkyl group which may have a substituent, an alkoxyalkyl group, an alkoxycarbonyl alkyl group, an alkoxyalkoxyalkyl group, an aminoalkyl group which may have a substituent, a saturated heterocyclic group which may have a substituent, an aralkyl group which may have a substituent, a benzocycloalkyl group which may have a substituent, or an alkyl group having a heterocyclic group which may have a substituent; $R^2$ represents an alkyl group; one of $R^3$ and $R^4$, which are different from each other, represents a hydrogen atom and the other represents a nitrile group, a carboxyl group, or an alkoxycarbonyl group; $R^5$ represents a monocyclic or ring-condensed aryl group which may have a substituent or a monocyclic or ring-condensed heteroaryl group which may have a substituent; X represents an oxygen atom or a sulfur atom; and one of $Q^1$, $Q^2$, and $Q^3$ represents a nitrogen atom and the other two represent CH; as well as a salt thereof, a hydrate thereof, or an N-oxide thereof.

2. A pharmaceutical composition containing a substituted vinylpyridine compound as described in claim 1, a salt thereof, a hydrate thereof, or an N-oxide thereof, as an active ingredient and a pharmaceutically acceptable carrier.

3. The pharmaceutical composition according to claim 2, wherein the active ingredient is present in phosphodiesterase IV inhibitor effective amounts.

4. The pharmaceutical composition according to claim 2, wherein the active ingredient is present in tumor necrotizing factor-α production inhibitory effective amounts.

5. A method for treatment of a disease caused by the enhancement of phosphodiesterase IV activity, comprising administering to a mammal an effective amount of a substituted vinylpyridine compound as described in claim 1, a salt thereof, a hydrate thereof, or an N-oxide thereof.

6. A method for treatment of a disease caused by the production of tumor necrotizing factor-α, comprising administering to a mammal an effective amount of a substituted vinylpyridine compound as described in claim 1, a salt thereof, a hydrate thereof, or an N-oxide thereof.

7. The method according to claim 5, wherein the mammal is a human.

8. The method according to claim 6, wherein the mammal is a human.

* * * * *